US010955411B2

(12) United States Patent
Apte et al.

(10) Patent No.: US 10,955,411 B2
(45) Date of Patent: Mar. 23, 2021

(54) MANIPULATION OF SAMPLE DROPLETS WITH AN ELECTRODE SYSTEM

(71) Applicant: PSOMAGEN, INC., Rockville, MD (US)

(72) Inventors: Zachary Apte, San Francisco, CA (US); Nathan Saichek, San Francisco, CA (US); Jessica Richman, San Francisco, CA (US)

(73) Assignee: PSOMAGEN, INC., Rockville, MD (US)

( * ) Notice: Subject to any disclaimer, the term of this patent is extended or adjusted under 35 U.S.C. 154(b) by 420 days.

(21) Appl. No.: 15/228,890

(22) Filed: Aug. 4, 2016

(65) Prior Publication Data

US 2017/0038368 A1 Feb. 9, 2017

Related U.S. Application Data

(60) Provisional application No. 62/201,001, filed on Aug. 4, 2015, provisional application No. 62/212,998, filed on Sep. 1, 2015.

(51) Int. Cl.
*G01N 33/551* (2006.01)
*G01N 33/543* (2006.01)
(Continued)

(52) U.S. Cl.
CPC .... *G01N 33/5438* (2013.01); *B01L 3/502792* (2013.01); *G01N 33/54326* (2013.01); *B01F 13/0069* (2013.01); *B01L 3/502707* (2013.01); *B01L 2200/0668* (2013.01); *B01L 2200/0673* (2013.01); *B01L 2300/0864* (2013.01);
(Continued)

(58) Field of Classification Search
CPC ......... B01L 3/502792; B01L 3/502707; B01L 2200/0668; B01L 2200/0673; B01L 2300/0864; B01L 2300/0867; B01L 2300/1827; B01L 2400/0427; B01L 2400/043; G01N 33/54326; G01N 33/5438; G01N 27/745; B01F 13/0069; B01F 13/0071; B01F 13/0076
See application file for complete search history.

(56) References Cited

U.S. PATENT DOCUMENTS 7,888,017 B2 2/2011 Quake et al.
8,093,064 B2 1/2012 Shah et al.
(Continued)

*Primary Examiner* — Christopher L Chin
(74) *Attorney, Agent, or Firm* — Morgan, Lewis & Bockius LLP

(57) ABSTRACT

A system and method for sample droplet processing, the system including a substrate, an electrode array network coupled to the substrate and configured to provide a pattern of controlled electric fields for manipulation of the set of sample droplets; a first layer in communication with the electrode array network, the first layer separating the electrode array network from fluid of the set of sample droplets; and a second layer opposing the first layer and displaced from the first layer to define a region wherein droplets of the set of sample droplets can reside. In some variations, the system can additionally include an electronics subsystem coupled to at least one of the substrate and the electrode array network, and a control module in communication with the electronics subsystem, wherein the control module generates and manipulates the pattern of controlled electric fields.

16 Claims, 20 Drawing Sheets

(51) Int. Cl.
*B01L 3/00* (2006.01)
*G01N 27/74* (2006.01)
*B01F 13/00* (2006.01)

(52) U.S. Cl.
CPC ............... *B01L 2300/0867* (2013.01); *B01L 2300/1827* (2013.01); *B01L 2400/043* (2013.01); *B01L 2400/0427* (2013.01); *G01N 27/745* (2013.01)

(56) References Cited

U.S. PATENT DOCUMENTS

| | | | |
|---|---|---|---|
| 8,349,276 B2 | 1/2013 | Pamula et al. | |
| 2006/0029955 A1* | 2/2006 | Guia | G01N 33/48728 435/6.11 |
| 2011/0059556 A1* | 3/2011 | Strey | B01L 3/502761 436/518 |
| 2013/0303394 A1 | 11/2013 | Wang et al. | |
| 2014/0197028 A1* | 7/2014 | Jacobs | B01L 3/502792 204/450 |
| 2014/0231257 A1* | 8/2014 | Bauer | B01L 3/502715 204/600 |
| 2015/0107998 A1* | 4/2015 | Fobel | G01N 27/44791 204/601 |
| 2015/0213193 A1 | 7/2015 | Apte et al. | |
| 2016/0110515 A1 | 4/2016 | Apte et al. | |
| 2016/0224748 A1 | 8/2016 | Apte et al. | |
| 2016/0224749 A1 | 8/2016 | Apte et al. | |
| 2016/0228003 A1 | 8/2016 | Apte et al. | |
| 2016/0230217 A1 | 8/2016 | Apte et al. | |
| 2016/0232280 A1 | 8/2016 | Apte et al. | |
| 2016/0232312 A1 | 8/2016 | Apte et al. | |
| 2016/0232313 A1 | 8/2016 | Apte et al. | |
| 2016/0232319 A1 | 8/2016 | Apte et al. | |
| 2016/0259909 A1 | 9/2016 | Apte et al. | |
| 2017/0024527 A1 | 1/2017 | Apte et al. | |

* cited by examiner (footprint of pads)

(footprint of pads)

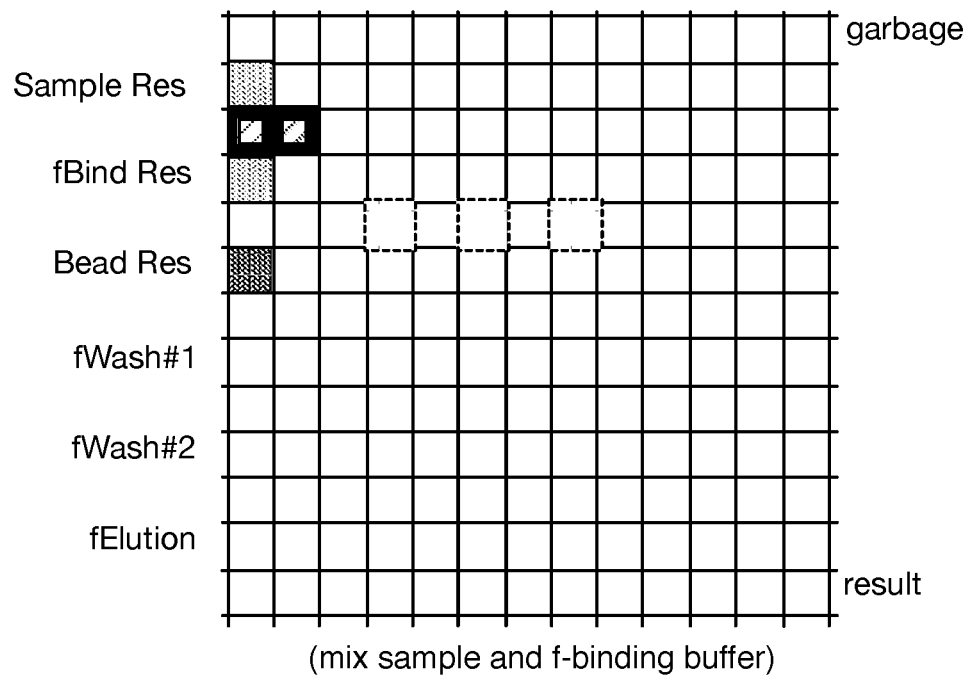
FIGURE 10C (mix sample and f-binding buffer)
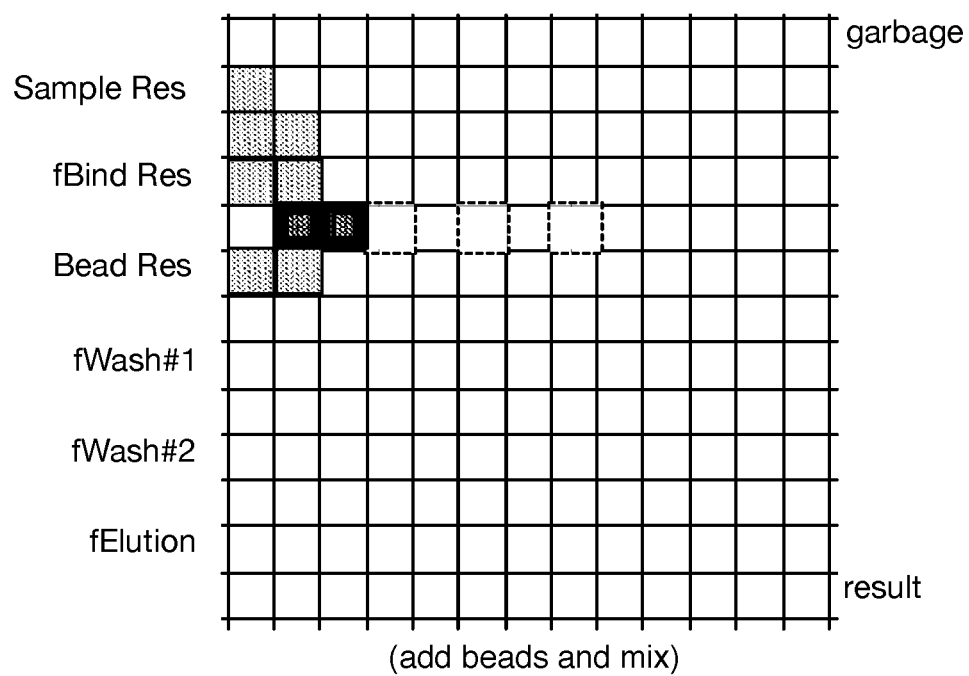
FIGURE 10D (add beads and mix)

(pull beads, discard liquid)

(add buffer 1 and mix)

(pull beads and discard liquid)

(add buffer 2 and mix)

(pull beads and discard liquid)

(repeat - add buffer 2 and mix)

(repeat - pul beads and discard liquid)

(dry beads at 65C)

(add elution buffer)

(hold warm at 65C for 10 minutes)

MANIPULATION OF SAMPLE DROPLETS WITH AN ELECTRODE SYSTEM

CROSS-REFERENCE TO RELATED APPLICATIONS

This application claims the benefit of U.S. Provisional Application Ser. No. 62/201,001 filed 4 Aug. 2015 and U.S. Provisional Application Ser. No. 62/212,998 filed on 1 Sep. 2015, which are each incorporated in its entirety herein by this reference.

TECHNICAL FIELD

This invention relates generally to the field of sample processing and more specifically to a new and useful digital microfluidics system and method in the field of sample processing.

BACKGROUND

Manipulation of sample fluids in a controllable manner can improve process flow and assay reliability in automated sample processing. Simultaneous manipulation of multiple samples can further be extremely useful in increasing the throughput of a process. While current systems can achieve simultaneous manipulation of multiple samples, such systems often implement complex fluid delivery systems that are prone to failure modes (e.g., clogging, sample cross contamination, etc.). Current systems and methods further typically process large sample volumes, while being incapable of processing small sample volumes (e.g., nanoliter volumes). In relation to processing of larger sample volumes, such systems and methods thus require larger spaces to accommodate equipment size, which limits the design of compact systems. Compactness is further a challenge in relation to performing a multi-step protocol for larger sample volumes in an automated manner. As such, current systems and methods for simultaneous and/or parallel processing of multiple fluid samples having small volumes can be improved in many areas.

There is thus a need in the field of sample processing for a new and useful digital microfluidics system and method. This invention creates such a new and useful system and method.

DESCRIPTION OF THE EMBODIMENTS

The following description of the embodiments of the invention is not intended to limit the invention to these embodiments, but rather to enable any person skilled in the art to make and use this invention.

1. System

Figure 1A:
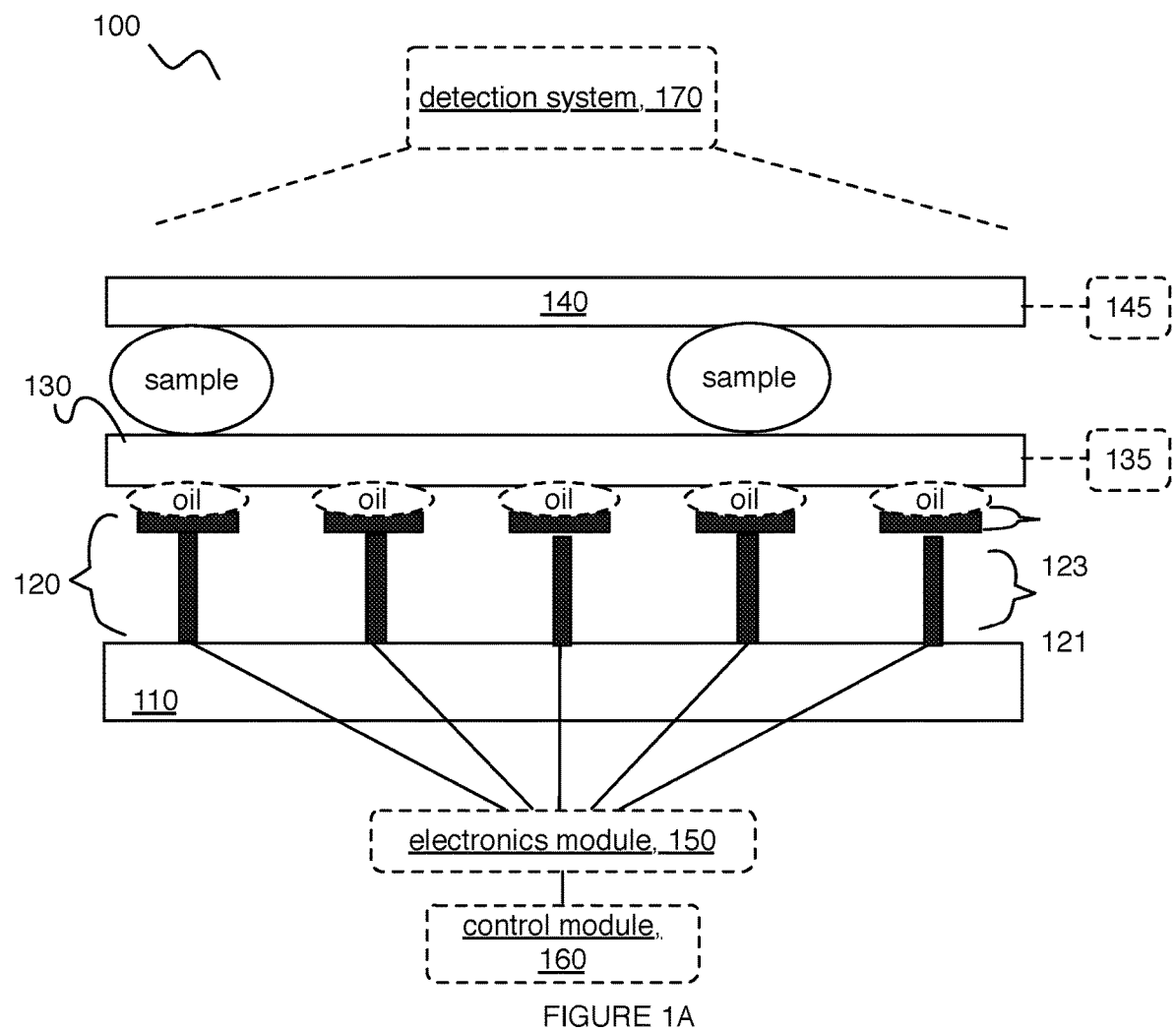
FIG. 1A depicts an embodiment of a digital microfluidics system.

As shown in FIG. 1A, an embodiment of a system 100 for processing a set of sample droplets includes: a substrate 110, an electrode array network 120 coupled to the substrate 110 and configured to provide a pattern of controlled electric fields for manipulation of the set of sample droplets; a first layer 130 in communication with the electrode array network 120, the first layer separating the electrode array network 120 from fluid of the set of sample droplets; and a second layer 140 opposing the first layer 130 and displaced from the first layer 130 to define a region wherein droplets of the set of sample droplets can reside. In some variations, the system 100 can additionally include an electronics subsystem 150 coupled to at least one of the substrate 110 and the electrode array network 120, and a control module 160 in communication with the electronics subsystem 150, wherein the control module generates and manipulates the pattern of controlled electric fields.

The system 100 functions to enable manipulation of small sample volumes from multiple samples in an automated or semi-automated manner, in increasing throughput of sample processing. The system further functions to prevent cross-contamination of samples, by implementing surfaces that prevent residual portions of a fluid sample at a location in the system from mixing with other samples. While embodiments and variations of the system 100 can be described as having a two-dimensional format, wherein sample volumes are manipulated within a two-dimensional plane, alternative variations of the system 100 can have a one-dimensional or a three-dimensional format, as described in more detail below.

In a specific application, the system 100 can facilitate processing of nanoliter volumes of biological samples simultaneously, in sequence, and/or in parallel, in a compact format. In more detail, the system 100 of the specific application can transport individual sample volumes, without cross-contamination, between different locations in the system 100 for storage, mixing (e.g., with processing reagent), reaction, and/or analysis in a rapid and automated format. For instance, specific examples of the system can include modules or units including one or more elements configured as described above, wherein each unit is configured to perform one or more specific sample droplet processing functions (e.g., magnetic separation, evaporation for fluid reduction, thermocycling, etc.). As such, the set of units can function as sample processing stations, wherein each unit can be configured to reversibly or irreversibly couple to one or more other units, such that outlets of upstream units couple to inlets of downstream units for sample processing.

Preferably, the system 100 is configured to automate or semi-automate protocols for processing samples with nucleic acid components (e.g., microbiome samples, diagnostic test samples, etc.). As such, the system can facilitate at least a portion of the method(s) described in U.S. application Ser. No. 14/593,424 entitled "Method and System for Microbiome Analysis" and filed on 9 Jan. 2015, which is herein incorporated in its entirety by this reference. Additionally or alternatively, variations of the system 100 can be configured to perform any other suitable method. Additionally or alternatively, variations of the system 100 can be used to support diagnostic tests for disease panels (e.g., respiratory disease panels, sexually-transmitted disease panels, etc.) and any other suitable biomarker-based test, where processing, detection, and quantification (i.e., relative quantification, absolute quantification) of a biocompound is desired.

In specific examples, diagnostic tests enabled using the system 100 can include tests for different identified health conditions and/or disease panels, wherein the identified health conditions and/or disease panels can be associated with at least one or more of: a neurological health condition, an autoimmune condition, an endocrine system condition, a mental health condition, a locomotor system condition, a metabolic (associated) disease condition, a cardiovascular disease condition, a cutaneous condition, a sexually transmitted disease, a dental health condition, a gastrointestinal health condition, and/or any other suitable condition, embodiments, variations, and examples of which are described in U.S. application Ser. No. 14/919,614 filed on 21 Oct. 2015, U.S. application Ser. No. 15/097,862 filed on 13 Apr. 2016, U.S. application Ser. No. 15/098,027 filed on 13 Apr. 2016, U.S. application Ser. No. 15/098,248 filed on 13 Apr. 2016, U.S. application Ser. No. 15/098,236 filed on 13 Apr. 2016, U.S. application Ser. No. 15/098,222 filed on 13 Apr. 2016, U.S. application Ser. No. 15/098,204 filed on 13 Apr. 2016, U.S. application Ser. No. 15/098,174 filed on 13 Apr. 2016, U.S. application Ser. No. 15/098,110 filed on 13 Apr. 2016, U.S. application Ser. No. 15/098,081 filed on 13 Apr. 2016, and U.S. application Ser. No. 15/098,153 filed on 13 Apr. 2016, which are herein incorporated in their entireties by this reference. In these specific examples, the system 100 can be used to provide qualitative information (e.g., positive test results, negative test results), quantitative information (e.g., quantitative parameter values associated with different detected or non-detected targets based on binding behavior), information associated with confidence in different sub-results of the diagnostic test (e.g., confidence ranges, indications of potential false positive results, indications of potential false negative results), information associated with non-conclusive results, and/or any suitable information related to each condition of the disease panel.

Additionally or alternatively, the system 100 can be used to provide information with health states not associated with diseases and/or be used for processing any other suitable sample with any other suitable process.

1.1 System—Substrate

The substrate 110 functions to provide support to other elements of the system 100. The substrate 110 can additionally function to transmit electrical current to the electrode array network 120 for generation of the pattern of controlled electric fields, by way of an electronics subsystem 150 (described in further detail below). As such, the substrate 110 preferably comprises regions composed of a semiconducting material (e.g., silicon, quartz, gallium arsenide) and/or a conducting material (e.g., gold, steel, platinum, copper nickel, silver, conductive polymer, etc.) supported by a laminate, but can additionally or alternatively comprise regions of an insulating or non-conductive material (e.g., glass, ceramic, polymer, etc.) in order to isolate regions of conductivity. In some variations, the substrate 100 can comprise a combination of materials (e.g., as in a composite, as in an alloy). Preferably, the substrate 100 has a uniform composition; however, the substrate 100 can alternatively have a non-uniform composition comprising regions or layers configured to provide any other suitable function (e.g., in relation to modulation of electric fields). In an example, the laminate of the substrate 110 can be composed of one or more of an epoxy (e.g., BT epoxy, CEM-1,5, etc.), an ester (e.g., cyanate ester), a paper-resin composite (e.g., FR-2, FR-4), a polyimide, polytetrafluoroethylene (PTFE), and/or any other suitable material. Furthermore, the substrate 130 can be rigid (e.g., composed of or otherwise supported by a rigid material) and additionally or alternatively comprise flexible regions for sample manipulation.

Figure 2A:
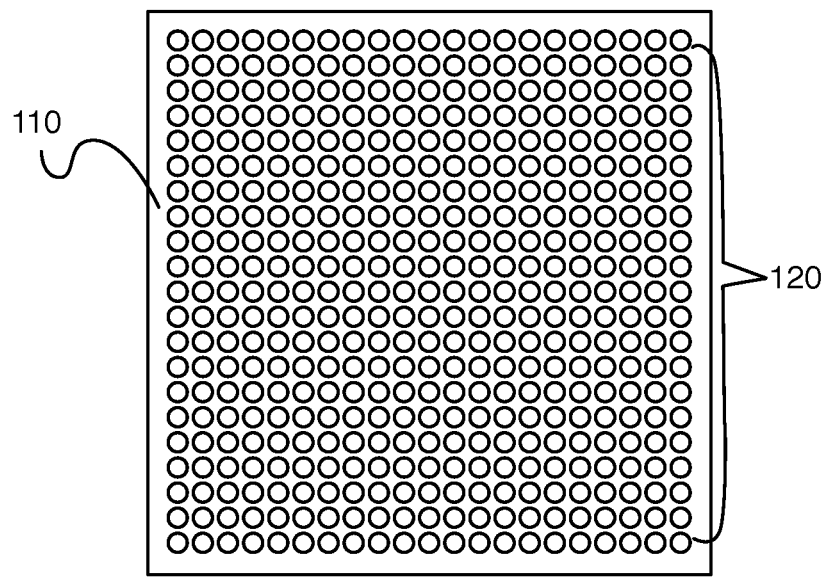
FIGS. 2A and 2B depict examples of a substrate in an embodiment of a digital microfluidics system.
Figure 2B:
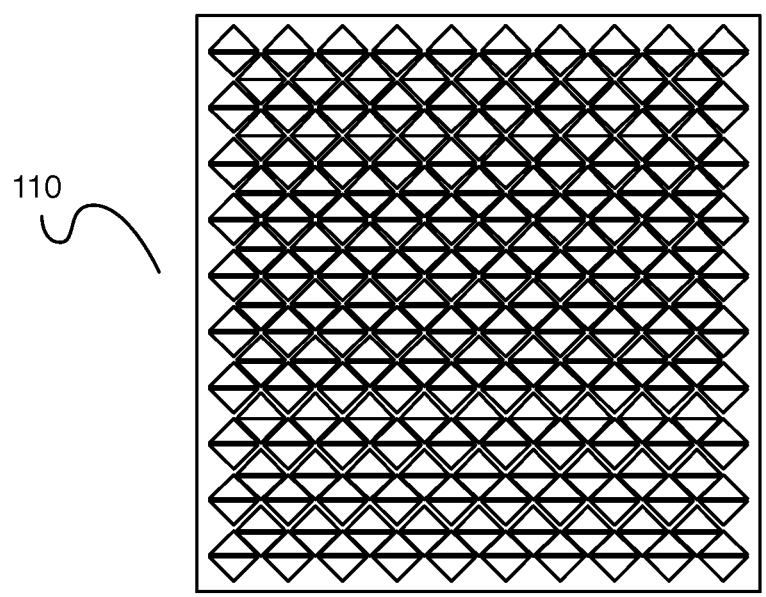
Figure 2C:
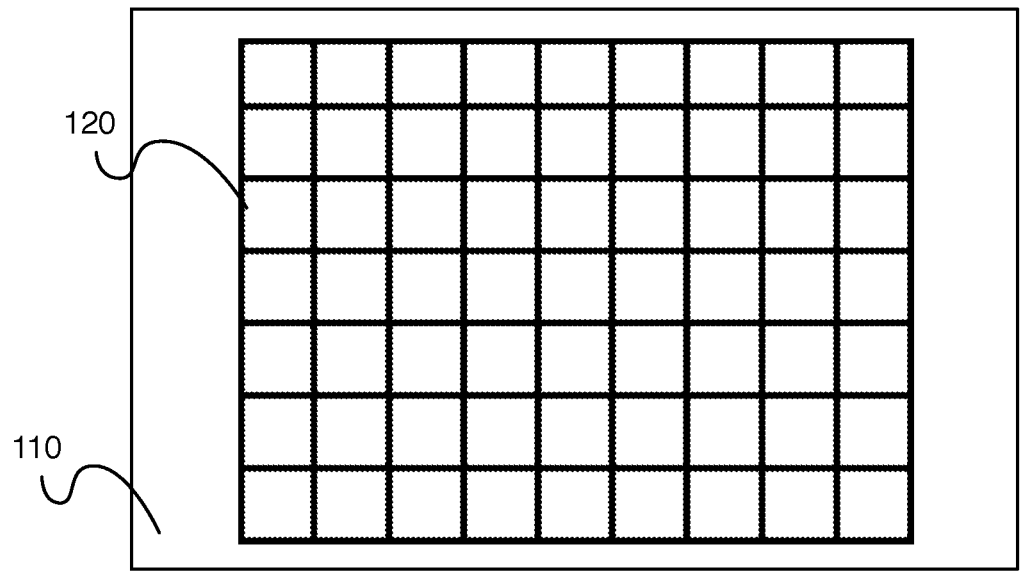
FIGS. 2C and 2D depict variations of a substrate and electrode array network in an embodiment of a digital microfluidics system.
Figure 2D:
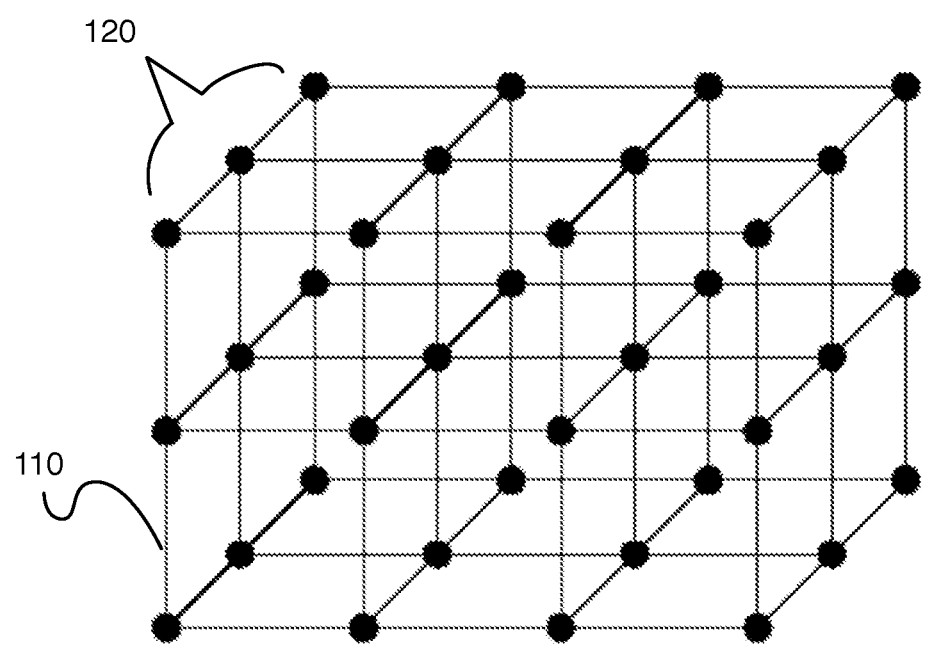

As shown in FIGS. 2A, 2B, and 2C, in a first variation, a 2D morphology of the substrate 110 can be substantially planar and continuous and have at least one broad surface (e.g., a pair of opposing broad surfaces); however, in variations alternative to the first variation, the substrate 110 can be non-planar and/or non-continuous (e.g., by including a network of openings across a broad planar or non-planar surface). For instance, a network of openings in the substrate 110 can correspond to or otherwise complement the configuration of the electrode array network 120. In a second variation, as shown in FIG. 2D, a 3D form of the substrate 100 can form a mesh (e.g., rectangular prismatic mesh, polygonal prismatic mesh, non-polygonal prismatic mesh, etc.) to which the electrode array network 120 can be coupled in facilitating manipulation of sample volumes. In variations of the above variations, either the 2D morphology or the 3D morphology of the substrate 110 can have one or more protrusions (e.g., walls, columnar formations, etc.) and/or recesses (e.g., pits) to which or into which the electrode array network 120 can be coupled for sample manipulation.

Preferably, the substrate 110 has dimensions that can fit within a 100 cm×100 cm×100 cm volumetric region, for purposes of compactness; however, the substrate 110 can additionally or alternatively have any other suitable dimensions.

In any of the above variations and examples, the substrate 110 can be processed using processing methods for rigid materials that are brittle or ductile (e.g., semiconductor processing methods, machining methods, printing methods, printed circuit board fabrication methods, etc.). Additionally or alternatively, at least some regions of the substrate can be processed using processing methods for flexible or otherwise compliant materials.

1.2 System—Electrode Array Network

The electrode array network 120 is in communication with at least one surface (e.g., broad surface, etc.) of the substrate 110 and functions to provide a pattern of controlled electric fields for manipulation of the set of sample droplets. The electrode array network preferably comprises a conductive material distributed at desired portions of the substrate 110 to create the pattern of the electrode array network. The pattern of the electrode array network 120 can thus be defined in space (e.g., in 2D space, in 3D space), but manipulation of the pattern of electric fields with the electrode array network 120 can also be performed in time, such that the pattern of electric fields generated using the electrode array network 120 is variable in time. In variations, the conductive material can be a conductive metallic material (e.g., copper, gold, nickel, etc.). Additionally or alternatively, the conductive material can comprise a composite material having one or more conductive components. For instance, the conductive material can include a conductive polymer and/or a conductive ink that can facilitate creation of an electric field at a desired location of the substrate 110. However, the material(s) of the electrode array network can additionally or alternatively comprise any other suitable material.

In providing communication between material of the electrode array network 120 and the substrate 110, the material of the electrode array network 120 can be coupled to the substrate 110 in any suitable manner. In one example, metallic pins (e.g., copper pins) can be coupled to the substrate 110 at one end of the pins, and metallic pads (e.g., copper pads) can be coupled to the opposite end of each pin, thereby facilitating generation of the controlled electric fields. In another example, conductive material (e.g., conductive ink, conductive polymer) can be printed onto the substrate 110 in a desired configuration. In other examples, patterns of conductive material can be coupled to the substrate 110 by one or more of: an etching process, a metal deposition process, a plating process (e.g., electroplating), a lithographic process, a transfer process, and any other suitable process that forms the electrode array network 110.

Figure 1B:
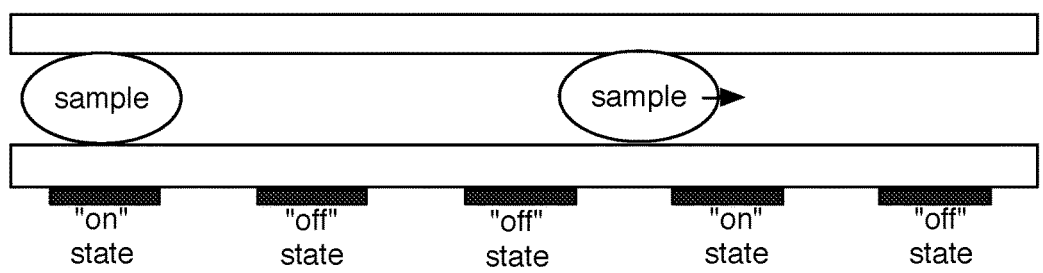
FIG. 1B depicts a variation of sample processing implemented by an embodiment of a digital microfluidics system.

The electrodes of the electrode array network 120 are preferably in communication with the electronics module 150 described in further detail below, such that each electrode and/or region of the electrode array network can be toggled between at least two voltage states for generation of the pattern of electric fields. As such, the substrate 110 can facilitate toggling of individual electrodes of the electrode array network 120, by enabling direct coupling between the electronics module 150 and electrodes of the electrode array network, to control transitioning of electrodes between different voltage states. As shown in FIG. 1B, the electrodes of the electrode array network 120 thus define active regions that can be toggled between different states for sample volume manipulation, such that sample volumes can be transmitted to and/or from the active regions by toggling of electrodes of the electrode array network between different voltage states.

The electrode array network 120 preferably comprises a set of pins 121 coupled to the substrate 110 at one end of each pin, and a set of pads 123 coupled to the opposite ends of the set of pins 121. The pins of the set of pins 121 thus preferably have an orientation that is substantially orthogonal relative to a broad surface of the substrate 110, and the set of pads 123 thus preferably define surfaces that are substantially parallel relative to the broad surface of the substrate 110, as shown in FIG. 1A. However, the set of pins 121 and the set of pads 123 can alternatively be structured in any other suitable configuration relative to a broad surface defined by the substrate 110.

Figure 4A:
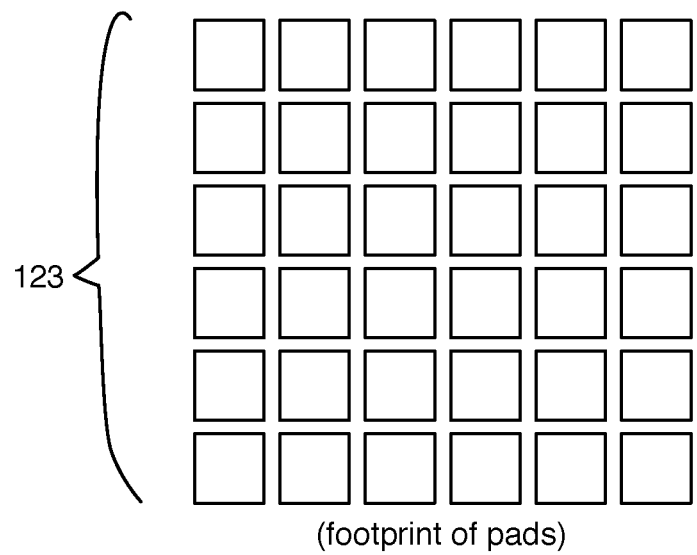
FIGS. 4A and 4B depict variations of pad configurations of an electrode array network in an embodiment of a digital microfluidics system.
Figure 4B:
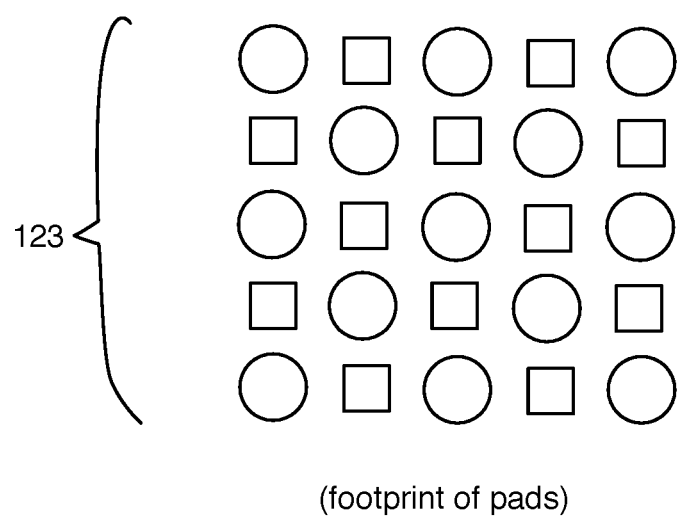

In more detail, each of the set of pads 123 can be identical in morphology to the other pads of the set of pads 123, in order to provide uniformity in field generation and sample manipulation, as shown in FIG. 4A. Alternatively, one or more pads of the set of pads 123 can be different in morphology than other pads in the set of pads, an example of which is shown in FIG. 4B, thereby introducing non-uniformity in field generation across the electrode array network. Variations in morphology of the set of pads 123 can, however, be configured in any other suitable manner to affect sample manipulation, as appropriate to applications of use of the system 100.

In a 2D format, the electrodes (i.e., pin-pad configurations) of the electrode array network 120 can be configured in an array, wherein each electrode or active region of the electrode array network is suitably spaced from the adjacent electrode(s) in a manner that allows sample volumes proximal to adjacent electrodes to maintain separation. In one variation of the 2D format, as shown in FIG. 2C, the electrodes/active regions of the electrode array network 120 can be arranged in a polygonal array (e.g., rectangular array, square array, etc.) with uniform spacing between electrodes/active regions. However, in alternative versions of this variation, the electrodes/active regions of the electrode array network 120 can alternatively be arranged with non-uniform spacing across the arrangement of electrodes. In this variation, one or more sample volumes of the set of sample droplets can thus be transmitted to different coordinates in 2D space (i.e., within a Cartesian coordinate system).

Figure 3:
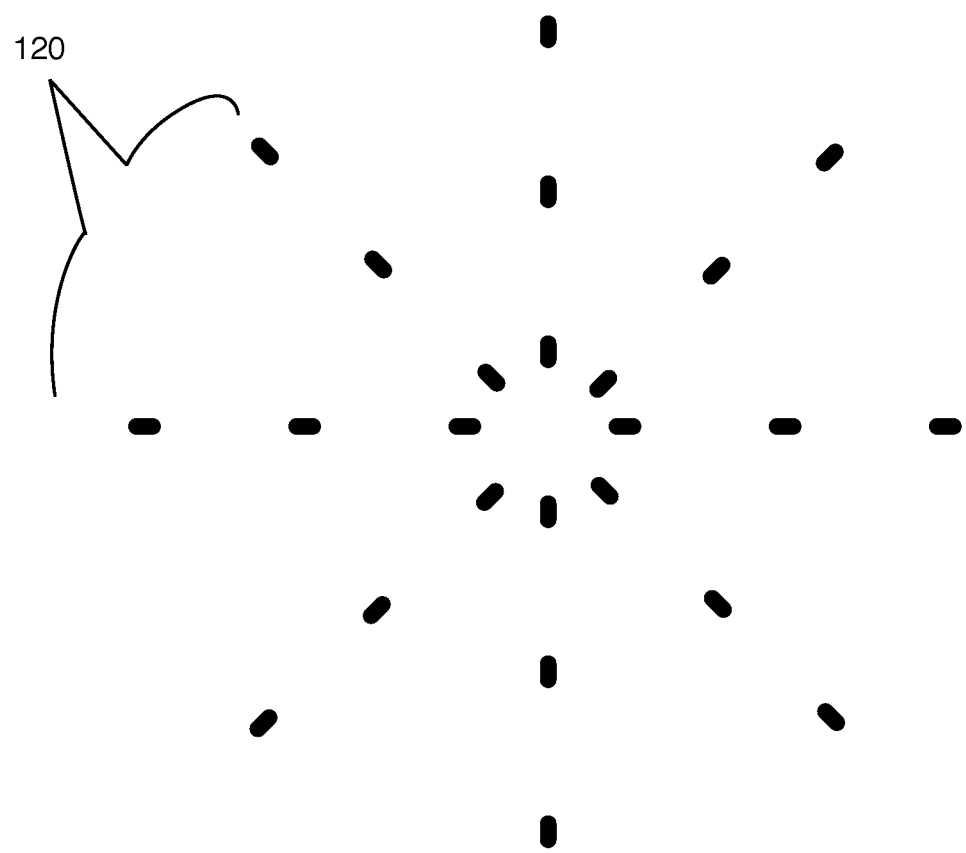
FIG. 3 depicts a variation of an electrode array network in an embodiment of a digital microfluidics system.

In another variation of a 2D format, as shown in FIG. 3, the electrodes/active regions of the electrode array network 120 can be arranged in a non-polygonal array (e.g., circular array, ellipsoidal array, etc.) with uniform spacing between electrodes/active regions. However, in alternative variations of this variation, the electrodes/active regions of the electrode array network 120 can alternatively be arranged with non-uniform spacing across the arrangement of electrodes. In this variation, one or more sample volumes of the set of sample droplets can thus be transmitted to different coordinates in 2D space (e.g., within a polar coordinate system). Two-dimensional formats of the electrode array network 120 can, however, be configured in any other suitable manner.

In a 3D format, the electrodes of the electrode array network 120 can be configured in a 3D array, wherein each electrode or active region of the electrode array network is suitably spaced from the adjacent electrode(s) in a manner that allows sample volumes proximal to adjacent electrodes to maintain separation. In one variation of the 3D format, as shown in FIG. 2D, the electrodes/active regions of the electrode array network 120 can be arranged in a polygonal prismatic array (e.g., rectangular prismatic array, cubical array, etc.) with uniform spacing between electrodes/active regions, in cooperation with the 3D morphology of the substrate described above. However, in alternative variations of this variation, the electrodes/active regions of the electrode array network 120 can alternatively be arranged with non-uniform spacing across the arrangement of electrodes. In this variation, one or more sample volumes of the set of sample droplets can thus be transmitted to different coordinates in 3D space (i.e., within a Cartesian coordinate system).

In another variation of a 3D format, the electrodes/active regions of the electrode array network 120 can be arranged in a non-polygonal prismatic or other 3D array (e.g., spherical array, cylindrical array, etc.) with uniform spacing between electrodes/active regions. However, in alternative variations of this variation, the electrodes/active regions of the electrode array network 120 can alternatively be arranged with non-uniform spacing across the arrangement of electrodes. In this variation, one or more sample volumes of the set of sample droplets can thus be transmitted to different coordinates in 3D space (e.g., within a polar coordinate system, within a cylindrical coordinate system). Three-dimensional formats of the electrode array network 120 can, however, be configured in any other suitable manner.

1.3 System—Sample Volume Contacting Surfaces

As shown in FIG. 1A, the electrode array network 120 is preferably in communication with a first layer 130, thereby isolating the electrode array network 120 from direct contact with sample volumes of the set of sample droplets. The first layer 130 thus functions to separate sample volumes from directly contacting the material of the electrode array network 120, and to prevent shorting of electrodes of the electrode array network 120. The first layer 130 can additionally or alternatively function to provide capacitive separation between the sample volumes and the electrode array network 120. The first layer 130 can be composed of a material that has insulating properties, such as a polymer material (e.g., polyvinyl chloride, polyethylene, polyimide, polyethylene terephthalate, etc.) or any other suitable material. Furthermore, the first layer 130 is preferably composed of a dielectric material that is insulating, but can be locally polarized by an applied electric field, upon activation of one or more electrodes of the electrode array network 120. As such, forces of electric fields generated upon activation of electrodes of the electrode array network 120 can be transmitted through the dielectric material of the first layer 130, for manipulation of sample volumes in contact with the first layer 130.

In locally polarizing the first layer 130 upon activation of electrodes of the set of electrodes 120, the first layer can be in communication with the set of electrodes by way of a layer of fluid material or other material situated between each pad of the set of pads 123 and the first layer 130 as shown in FIG. 1A, wherein the material facilitates field generation at the first layer 130 in a controlled manner. The material is preferably isolated to the pad region(s), such that the material does not directly couple electrode pads to each other directly. However, the material can alternatively not be isolated to the pad region(s) and couple multiple electrode pads to each other directly. The material can have any suitable fluid properties, in relation to one or more of: hydrophobicity, viscosity, thermal conductivity, electrical conductivity, viscoelasticity, wettability, density, electrical stimulus responsiveness, and/or any other suitable properties. For instance, in one variation, material between the electrode array network 120 and the first layer 110 can function to conduct heat from a heating element proximal a pad of the electrode array network 120 through the first layer 130 and toward a sample droplet. In another variation, material between the electrode array network 120 and the first layer 110 can function to modulate electric field characteristics between a pad of the electrode array network 120 and a sample droplet at the first layer 110. In still another variation, the material can be configured to deform under a stimulus (e.g., an electrical current, provided heat, etc.) in order to transmit a stimulus (e.g., a force, thermal stimulus, etc.) to a sample droplet at the firsts layer 110. However, the material between the electrode array network 120 and the first layer 110 can additionally or alternatively have any other suitable function.

In variations, the material between the electrode array network 120 and the first layer 130 can be one or more of: a hydrophobic fluid (e.g., an oil), a hydrophilic fluid, a polymer (e.g., a hydrogel), a metal, a semi-conducting material, a ceramic, a non-conductive material layer (e.g., an adhesive layer, a resin layer, etc.), and any other suitable material. In a specific example, as shown in FIG. 1A, the material comprises an oil; however, variations of the specific example can alternatively comprise any other suitable material (e.g., adhesive, resin, etc.). However, the first layer 130 can additionally or alternatively be in communication with the set of electrodes 120 in any other suitable manner. As such, some variations of the system 100 can omit a material coupling the electrode array network 120 to the first layer 130.

In one variation, the first layer 130 can be a flexible layer that is applied over the set of pads 123 of the set of electrodes 120 prior to each use of the system 100, thereby avoiding sample cross-contamination or any other suitable form of contamination.

As such, in some variations, the system can include a first layer providing subsystem 135, as shown in FIG. 1A, that includes a length of first layer material, wherein the first layer providing subsystem 135 transmits a sub-length of the length of first layer material into position relative to the electrode array network in between runs of the system 100. In one variation, the first layer providing subsystem 135 can include a spool of rolled first layer material positioned at a first side of the electrode network array 120, wherein the first layer material can be unrolled into position between runs of the system 100, and wherein a terminal region of the first layer material being unwound is anchored at a position opposite the first side of the electrode network array 120 (e.g., as in a scrolling mechanism with a dispensing spool and a collecting spool). In another variation, the first layer providing subsystem 135 can include a folded length (e.g., accordion folded length) of first layer material that can be unfolded into position between runs of the system 100. In another variation, the first layer providing subsystem 135 can include layers or sheets of first layer material that are dispensed into position between runs of the system. However, variations of the first layer providing subsystem 135 can alternatively implement any other suitable configuration or dispensing mechanism. Furthermore, dispensing by the first layer providing subsystem 135 can be automatic (e.g., using a controller coupled to an actuator of the first layer providing subsystem 135 that dispenses the first layer material into position); however, dispensing by the first layer providing subsystem 135 can alternatively be manual (e.g., conducted by an operator of the system 100).

In a specific example, the first layer 130 can be unrolled from a rolled sheet of material of the first layer 130 as dispensed from a first layer providing subsystem including a spool, and directly applied over the set of electrodes 120 prior to a sample run. Then, after the sample run is complete, the used first layer 130 can be discarded (e.g., with an automatic cutter, by winding used first layer material about an opposing spool that collects used material, etc.), and a new first layer 130 can be unrolled from the rolled sheet of material of the first layer 130 and applied over the set of electrodes 120. As such the first layer 130 can be easily replaced between runs of the system 100, by using a disposable first layer 130 in combination with reusable components of the system 100 (e.g., of a first layer material providing subsystem). However, variations of the first layer 130 can be brought into communication with the set of electrodes in any other suitable manner, and disposable/reusable aspects of the system 100 can be configured in any other suitable manner.

The first layer 130 preferably has a constant thickness relative to the substrate 100/electrode array network 120, such that the fields generated about each electrode are uniform. However, the first layer 130 can alternatively be configured with any suitable distribution of thickness, in order to create variations in field strength across the first layer 130 (e.g., in relation to different volumes of a sample, in relation to combination of sample volumes with process reagents, etc.). In the example shown in FIG. 1A, the first layer 130 has a constant thickness relative to the substrate 110, and is in communication with the electrode array network 120 by way of layers of oil (or other suitable material as described) between pads of the electrode array network 120 and the first layer 130. However, variations of the example shown in FIG. 1A can alternatively be configured in any other suitable manner.

Additionally, the first layer 130 preferably is composed of or is treated (e.g., coated) with a hydrophobic material at regions contacting sample volumes of the set of sample droplets, wherein the hydrophobic material is configured to increase the contact angle (i.e., decrease wettability) of the first layer 130. As such, coupling of the hydrophobic material to the first layer 130 primarily prevents retention of residues from the sample volumes at the first layer 130, in stopping sample cross-contamination or other types of contamination. Preferably, the hydrophobic material does not adversely interfere with electric fields generated by the electrode array network 120 and transmitted through the first layer 120, and further does not contaminate samples processed by the system 100; however, the hydrophobic material and/or other layers coupled to the first layer 130 can alternatively have any suitable field modulating effect. In variations, the hydrophobic material can be sprayed onto or otherwise applied to surfaces of the first layer 130 intended to contact samples processed with the system 100. In specific examples, the hydrophobic material can comprise a superhydrophobic material including one or more of: a polysiloxane-derived material (e.g., polydimethylsiloxane, Rainex™), a perfluoroalkyl-derived material, a perfluoropolyether-derived material, and any other suitable material.

Additionally or alternatively, modulation of the hydrophobicity of the first layer 130 can be facilitated by way of an applied electric field (e.g., with the electrode array network 120), wherein without an applied field, the first layer 130 is hydrophobic, but with an applied electric field, the first layer 130 transitions to a hydrophilic state (i.e., due to enhanced polarity of the first layer 130). In examples, the first layer 130/hydrophobic material can be composed of glass and/or a polymer material (e.g., polytetrafluoroethylene, perfluoroalkane, perfluoropolyether, etc.). However, in variations of these examples, the first layer can alternatively be composed of any other suitable material.

While variations of a disposable first layer 130 are described above, the first layer 130 can alternatively be directly coupled about the electrode array network 120 and directly coupled to the substrate 100, in generating a seal about the electrode array network 120 in a variation wherein the first layer 130 is reusable. Coupling between the first layer and the electrode array network 120/substrate 110 can be provided by way of a bonding process (e.g., thermal bonding process, in variations wherein the substrate 110 and the first layer 130 are compatible for thermal bonding). Additionally or alternatively, coupling between the first layer 130 and the electrode array network 120/substrate 110 can be provided by way of one or more of: an adhesive binding process, a dipping and curing process, a deposition process, and any other suitable process.

In examples of a first layer 130 that is directly coupled about the electrode array network 120, the first layer 130/hydrophobic material can be composed of an oxide (e.g., indium tin oxide), glass, and/or a polymer material (e.g., polytetrafluoroethylene, perfluoroalkane, perfluoropolyether, etc.). The first layer 130 can, however, be composed of any other suitable material.

As shown in FIG. 1A, the system 100 can include a second layer 140 that opposes the first layer 130 and is displaced from the first layer 130, in order to define a region wherein sample volumes (e.g., nanoliter droplets) of the set of sample droplets can reside. Isolating the sample volumes of the set of sample droplets between the first layer 130 and the second layer 140 further functions to prevent evaporative loss of portions of the set of sample droplets during processing, which can affect analyses (e.g., quantitative analyses) of the sample volumes. However, some variations of the system 100 (e.g., a unit of the system) can alternatively omit a second layer 140 in order to provide controlled evaporation of sample droplets, as described in further detail below.

In providing separation between the first layer 130 and the second layer 140, the second layer 140 can be supported by a frame or other suitable structure that allows a gap region to form between the first layer 130 and the second layer 140. In these variations, the frame is preferably coupled to and confined to peripheral regions of the substrate 110 in a manner that does not interfere with sample transmission throughout the system 100; however, the frame can additionally or alternatively be configured relative to the substrate 110, the first layer 130, and the second layer 140 in any other suitable manner. However, as described in more detail below, variations of the system 100 can alternatively omit a second layer 140, which can allow larger sample volumes to be processed and/or enable any other suitable application.

Similar to the first layer 130, the second layer 140 is preferably composed of a dielectric material that has insulating properties, but can be locally polarized by an applied electric field, upon activation of one or more electrodes of the electrode array network 120. As such, forces of electric fields generated upon activation of electrodes of the electrode array network 120 can enable manipulation of sample volumes in contact with the second layer 140 and the first layer 130. Alternatively, the second layer 140 can be composed of an insulating material that lacks or otherwise has weak dielectric properties. Preferably, the second layer 140 is substantially rigid; however, the second layer 140 can alternatively be flexible in order to enable manipulation of the second layer 140 relative to the first layer.

As such, in some variations, the system 100 can include a second layer providing subsystem 145, as shown in FIG. 1A, that includes a length of second layer material, wherein the first layer providing subsystem 145 transmits a sublength of the length of second layer material into position relative to the electrode array network 120 in between runs of the system 100. In one variation, the second layer providing subsystem 145 can include a spool of rolled second layer material positioned at a first side of the electrode network array 120, wherein the second layer material can be unrolled into position between runs of the system 100, and wherein a terminal region of the second layer material being unwound is anchored at a position opposite the first side of the electrode network array 120 (e.g., as in a scrolling mechanism with a dispensing spool and collecting spool). In another variation, the second layer providing subsystem 145 can include a folded length (e.g., accordion folded length) of second layer material that can be unfolded into position between runs of the system 100. In another variation, the second layer providing subsystem 145 can include layers or sheets of second layer material that are dispensed into position between runs of the system. However, variations of the second layer providing subsystem 145 can alternatively implement any other suitable configuration or dispensing mechanism. Furthermore, dispensing by the second layer providing subsystem 145 can be automatic (e.g., using a controller coupled to an actuator of the first layer providing subsystem 145 that dispenses the second layer material into position); however, dispensing by the second layer providing subsystem 145 can alternatively be manual (e.g., conducted by an operator of the system 100).

In relation to the first layer providing subsystem 135, the second layer providing subsystem 135 can be configured to coordinate dispensing of the second layer 140 with the first layer 130, such that both the first layer 130 and the second layer 140 are dispensed into position in a coordinated manner in between runs of the system. For instance, both layers 130, 140 can be dispensed at the same rate from their respective dispensing spools and discarded first and second layer material can be collected at collecting spools in between runs of the system 100. However, variations of coordinated dispensing can be configured in any other suitable manner.

In a specific example, the second layer 140 can be unrolled from a rolled sheet of material of the first layer 140 as dispensed from a first layer providing subsystem including a spool, and directly applied over the set of electrodes 120 prior to a sample run. Then, after the sample run is complete, the used second layer 140 can be discarded (e.g., with an automatic cutter, by winding used second layer material about an opposing spool that collects used material, etc.), and a new second layer 140 can be unrolled from the rolled sheet of material of the second layer 130 and applied over the first layer 130. As such the second layer 140 can be easily replaced between runs of the system 100, by using a disposable second layer 140 in combination with reusable components of the system 100 (e.g., of a second layer material providing subsystem). However, variations of the first layer 140 can be brought into position relative to the first layer 130 in any other suitable manner, and disposable/reusable aspects of the system 100 can be configured in any other suitable manner.

The second layer 140 preferably has a constant thickness, in order to provide a uniform gap between the first layer 130 and the second layer 140. However, the second layer 140 can alternatively be configured with any suitable distribution of thicknesses, in order to modulate the gap width between the first layer 130 and the second layer 140. In the example shown in FIG. 1A, the second layer 130 has a constant thickness, and is coupled to the substrate 110 by way of a frame that provides constant displacement between the first layer 130 and the second layer 140.

Additionally, and similar to the first layer 130, the second layer 140 is preferably coated with a hydrophobic material at regions contacting sample volumes of the set of sample droplets, wherein the hydrophobic material is configured to increase the contact angle (i.e., decrease wettability) of the second layer 140. As such, coupling of the hydrophobic material to the second layer 140 primarily prevents retention of residues from the sample volumes at the second layer 140, in stopping sample cross-contamination. Preferably, the hydrophobic material does not adversely interfere with electric fields generated by the electrode array network 120 for manipulation of the set of sample droplets, and further does not contaminate samples processed by the system 100; however, the hydrophobic material and/or other layers coupled to the second layer 140 can alternatively have any suitable field modulating effect. Additionally or alternatively, modulation of the hydrophobicity of the second layer 140 can be facilitated by way of an applied electric field (e.g., with the electrode array network 120), wherein without an applied field, the second layer 140 is hydrophobic, but with an applied electric field, the second layer 140 transitions to a hydrophilic state (i.e., due to enhanced polarity of the first layer 130). In variations, the hydrophobic material can be sprayed onto or otherwise applied to surfaces of the first layer 130 intended to contact samples processed with the system 100. In specific examples, the hydrophobic material can comprise a superhydrophobic material including one or more of: a polysiloxane-derived material (e.g., polydimethylsiloxane, Rainex™), a perfluoroalkyl-derived material, a perfluoropolyether-derived material, and any other suitable material.

In examples of a rigid second layer 140, the second layer 140/hydrophobic material can be composed of an oxide (e.g., indium tin oxide), glass, and/or a polymer material (e.g., polytetrafluoroethylene, perfluoroalkane, perfluoropolyether, etc.). In examples of a flexible second layer 140, the second layer 140 can be composed of a flexible polymer, as described above, such as polyvinyl chloride (e.g., Saran™ wrap). The second layer 140 can, however, be composed of any other suitable material.

In some variations, the second layer 140 can include a port or opening into the region between the first layer 130 and the second layer 130, wherein the port allows one or more volumes of the set of sample droplets to be distributed into the system 100 for manipulation and sample processing. The port can be peripherally located proximal an edge of the second layer 140, or can alternatively be located at any other suitable portion of the second layer 140 for transmission of a sample into the region between the first layer 130 and the second layer 140. In other variations, the system 100 can comprise one or more ports or openings configured at one or more of the first layer 130, the second layer 140, and the substrate 110, in enabling sample transmission into the region between the first layer 130 and the second layer 130. Furthermore, either of the first layer 130 and the second layer 140 can be transparent or translucent, in enabling detection of positions of the sample volumes within the system 100, or enabling optical-based analyses of samples within the system 100 to be performed.

While the above description of the first and the second layers 130, 140 generally applies to 2D formats of the system, variations of the elements can be adapted to a 3D format. For instance, in a variation wherein the substrate 110 defines a 3D mesh with electrodes positioned at nodes of the mesh, the substrate 110 and electrodes of the electrode array network 120 can be encapsulated in dielectric material (or other insulating material) as the first layer 130/second layer 140 that prevents residue retention and provides an electric field for sample manipulation. Other formats of the system 100 can, however, be configured in any other suitable manner.

The system 100 can thus include any additional elements and/or omit any of the above described elements (e.g., the first layer 130, the second layer 140) as appropriate for different sample processing applications.

1.4 System—Supporting Elements

In some variations, the system 100 can additionally include an electronics module 150 coupled to at least one of the substrate 110 and the electrode array network 120. Additionally, the system 100 can include a control module 160 in communication with the electronics module 150, wherein the control module generates and manipulates the pattern of controlled electric fields. The electronics module 150, in cooperation with the control module 160 thus function to power the system 100 and modulate voltage states at each of the set of electrodes of the electrode array network 120. The electronics module 150, in cooperation with the control module 160, is preferably configured to detect voltage states of each of the electrodes of the electrode array network, in order to correctly toggle the electrodes of the electrode array network between different states. Furthermore, electronics module 150 can provide power regulation functions for the system 100. Preferably the control module 160 generates and governs the pattern of electric fields produced in the system, in transmitting the samples between different locations of the system 100. As such, the control module 160 can receive information indicative of positions of the sample volumes within the system 100, in ensuring that sample volumes do not collide and cross-contaminate within the system 100. Information indicative of positions of the sample volumes can be generated by way of a detection system 170, described in more detail below.

Figure 6:
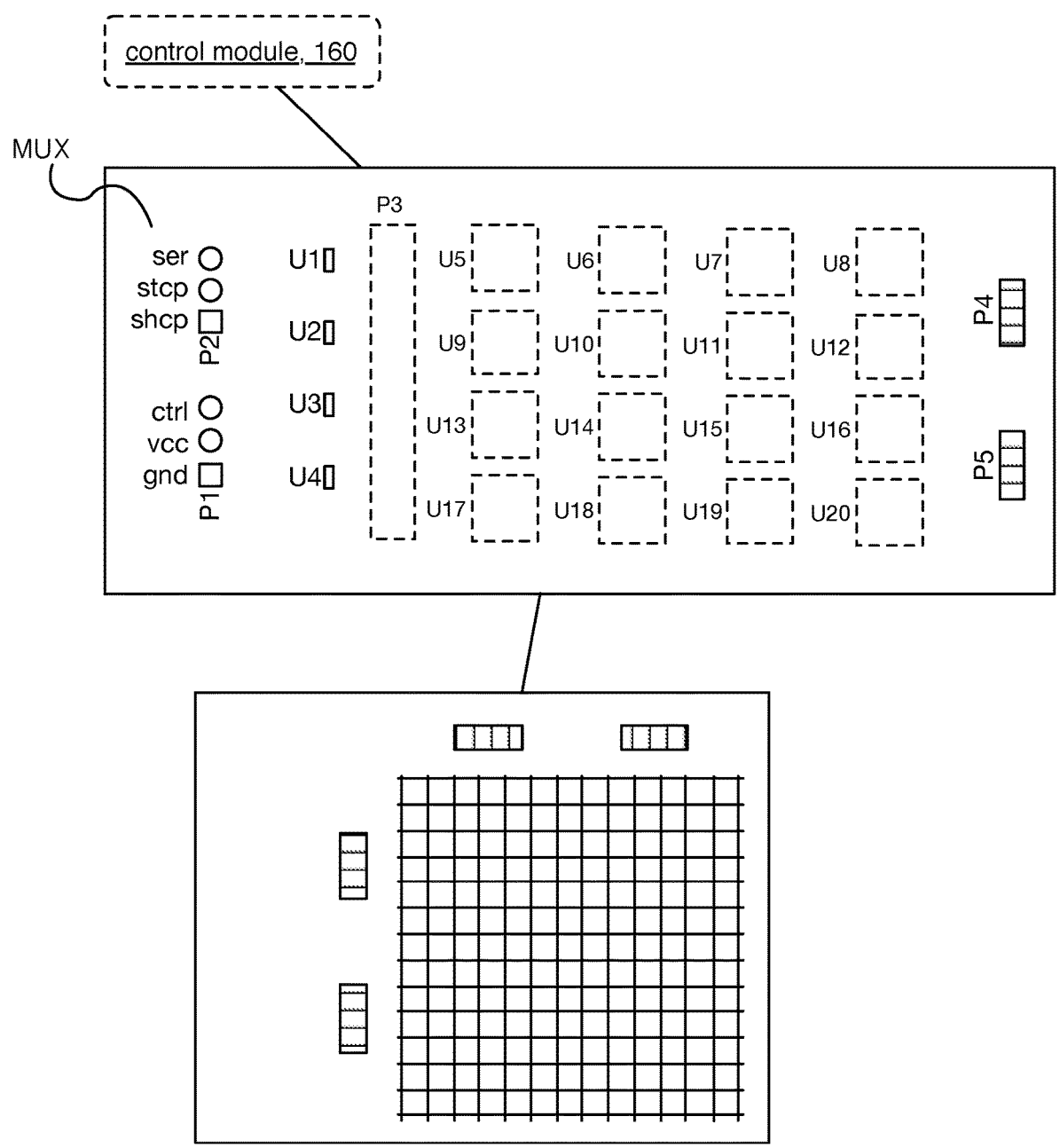
FIG. 6 depicts examples of additional elements associated with the digital microfluidics system.

In one variation, The control module 160 can be coupled to one or more multiplexers (MUXs), an example of which is shown in FIG. 6, that interface with the substrate 110 by way of one or more ports, wherein the ports provide electrical coupling between the MUXs and pins of the electrode array network 120. As such, a multiplexed configuration can be used to manipulate one or more electrode positions of the electrode array network 120.

As noted above and shown in FIG. 1A, the system 100 can further include a detection system 170, wherein the detection system 170 functions to identify positions of sample volumes within the system 100, in providing information to the control module 160 (or other control/processing modules associated with the system). As such, information generated by the detection system 170 prevents cross-contamination of different samples, and enables samples to be combined with process reagents according to desired protocols for sample processing. In one variation, the detection system 170 can comprise one or more optical sensors (e.g., of a camera), wherein the optical sensor(s) are configured to have all potential positions of the sample volumes within view. As such, this variation enables optical detection of positions of the sample volumes. In another variation, a set of force sensors can be in communication with at least one of the first layer 130 and the second layer 140, in detecting forces (e.g., mass-derived forces) provided by a sample at a position within the system. In another variation, the detection system 170 can include a module configured for ultrasonic sensing of positions of the sample volumes within the system 100. In yet another variation, the detection system 170 can include a module configured for capacitance sensing of positions of the sample volumes within the system 100. The detection system 170 can, however, be configured in any other suitable manner and/or comprise any other suitable modules for detection of positions of the sample volumes within the system 100.

Additionally or alternatively, variations of the optical detection system 170 can include one or more filters for transmitting light at an emission wavelength (or range of emission wavelengths) to one or more samples for fluorescence excitation and/or light at an excitation wavelength (or range of excitation wavelengths) from one or more excited samples to a detection sensor, in order to enable fluorescent detection assays. In relation to the filters, the optical detection system 170 can thus include any suitable configuration of optical components (e.g., beam shaping elements, mirrors, filters, lenses, etc.) for transmitting light to and/or from samples to components of the optical detection system 170.

Figure 7A:
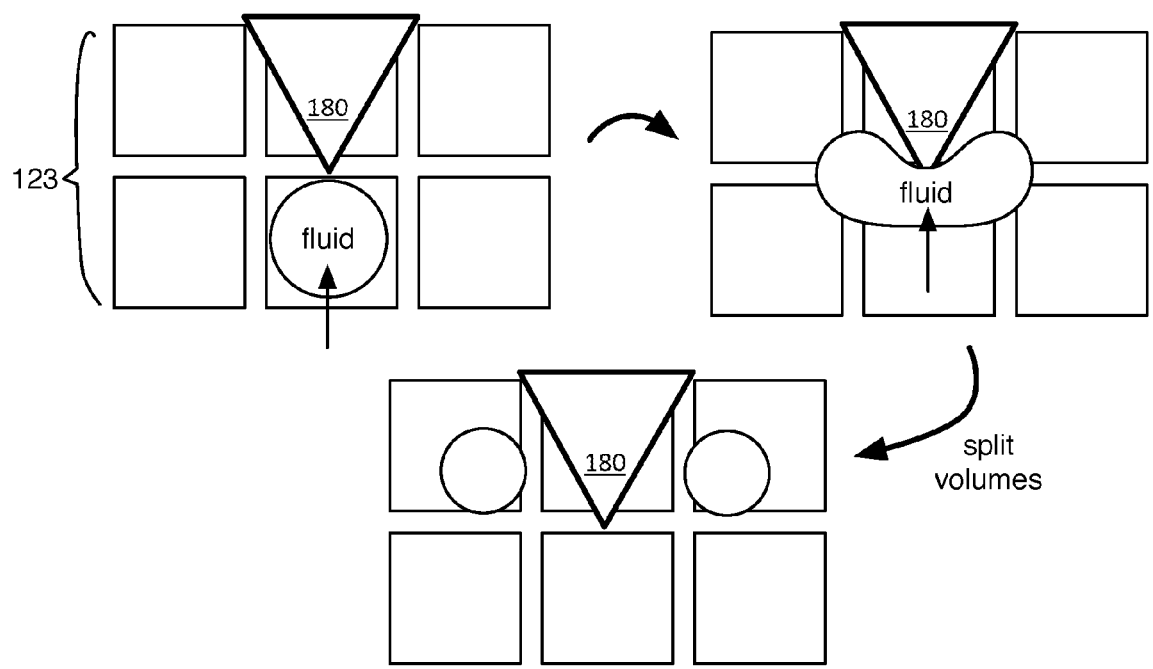
FIG. 7A depicts a variation of a wedge element for fluid splitting, in an embodiment of a digital microfluidics system.

In some variations, as shown in FIG. 7A, the system 100 can include a wedge element 180 configured to physically split fluid volumes during sample processing. In variations wherein the system 100 is closed, the wedge element 160 can be configured between the first layer 130 and the second layer 140, such that driving a fluid volume toward a pointed region of the wedge element 180, upon activation of one or more electrode positions of the electrode array network 120, physically splits the fluid volume into at least two portions. In variations, the wedge element 180 can include any suitable number of pointed regions (in generating one or more split volumes), and can be configured in any suitable orientation relative to other elements of the system 100, in splitting fluid volumes in any desired manner.

The system 100 can, however, include any other suitable components for manipulating sample volumes in any other suitable manner.

1.5 System—Modules

Figure 7B:
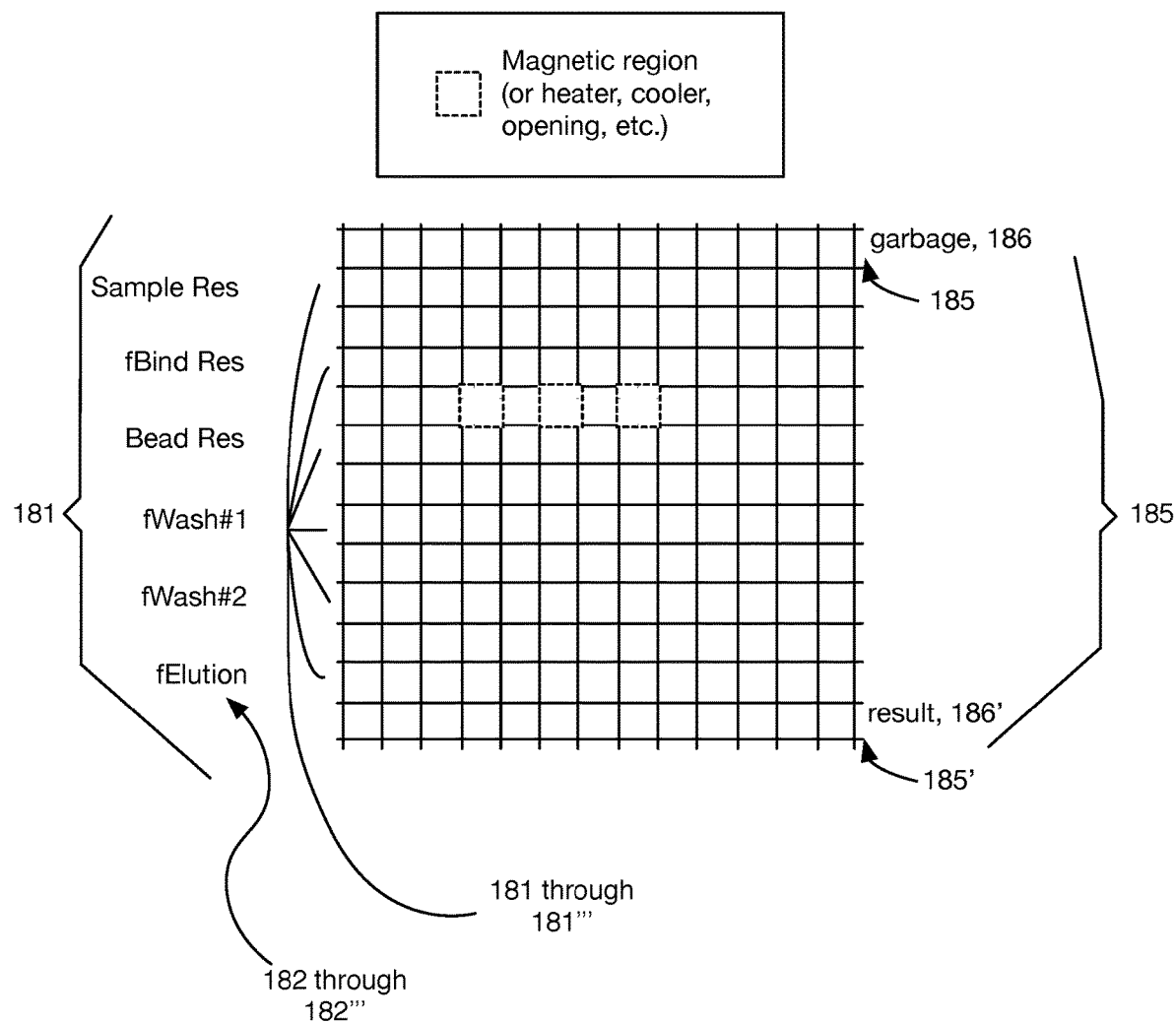
FIG. 7B depicts a variation of a unit of a digital microfluidics system.

While one unit of the system 100 is described above, modules of the system 100 can be adapted for any of a set of protocol steps or applications. For instance, one module of the system 100 can include a magnet (e.g., a permanent magnet, an electromagnet) proximal one or more electrode positions of the set of electrodes of the module, wherein the magnet provides a magnetic field for manipulating sample components. In variations including an electromagnet, the electromagnet can be transitioned from activated and deactivated states, in order to control aspects of sample processing requiring a magnetic field. In specific applications, the magnetic field can be used for magnetic separation (e.g., of waste components from target components using magnetic particles with moieties configured for binding to targets of samples) or for any other suitable purpose. In a specific example, as shown in FIG. 7B a magnetic separation unit can include three separate magnets configured proximal three central positions of the electrode array network 120 (e.g., at the first layer 130, at the second layer 140), for magnetic separation of nucleic acid material from sample components. However, variations of the specific example can be configured in any other suitable manner (e.g., in relation to number of magnets, strength of magnets, and/or position of magnets).

Figure 8:
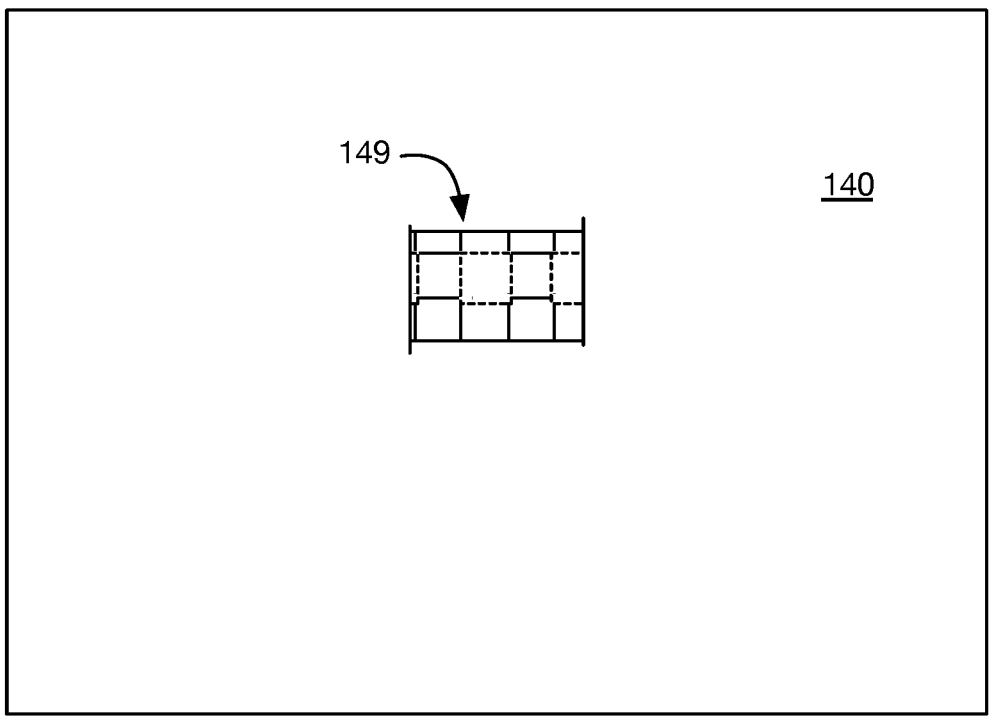
FIG. 8 depicts a variation of an evaporation unit of a digital microfluidics system.

Additionally or alternatively, one module/unit of the system 100 can be an open module that has a first layer 130 but omits a second layer 140, which can function to allow for sample evaporation (e.g., during drying) and/or for processing of larger sample volumes. In one variation of this unit of the system, the unit can comprise a second layer 140 having an opening 149, as shown in FIG. 8, that spans multiple positions of the electrode array network 120, such that one or more sample droplets can be transmitted into the opening 149 to initiate evaporation, and then transmitted away from the opening 149 to stop an evaporation process. However, variations of the unit can be configured in any other suitable manner.

Additionally or alternatively, one module/unit of the system 100 can be a closed system 100 that includes both a first layer 130 and a second layer 140, in order to prevent evaporative loss of a sample volume during a stage of processing, to provide finer control of the sample environment, and/or to serve any other suitable purpose.

In relation to open and closed modules, the system 100 can be configured to drive fluid volumes under a second layer 140 into a closed environment, or alternatively to drive fluid volumes from under a second layer 140 into an open environment. Additionally or alternatively, apparatus associated with the system 100 can be configured to transmit a second layer 140 toward an open module, thereby transitioning the open module to a closed module and back to an open module in a reversible manner.

Additionally or alternatively, one module of the system 100 can include a heating element (e.g., Peltier heating element) proximal one or more electrode positions of the electrode array network 120, as shown in FIG. 7B, thereby forming a heating region (e.g., for inducing a pH shift during sample processing, for incubating a sample volume, for drying a sample volume, etc.) at the module. Variations of the heating module/unit can be combined with an open unit omitting a second layer 140 or otherwise having an opening in its second layer 140, in order to enhance evaporation effectiveness. However, variations of the units of the system 100 described above can alternatively be combined in any other suitable manner.

Additionally or alternatively, one module of the system 100 can include a cooling element (e.g., fan, Peltier cooling element) proximal one or more electrode positions of the electrode array network 120, as shown in FIG. 7B, thereby forming a cooling region at the module.

Additionally or alternatively, modules of the system 100 can be configured to serve any other suitable purpose. Furthermore, functional aspects of one or more modules can be combined in any other suitable manner to produce modules with multiple types of functionality.

Furthermore, in relation to the units, as shown in FIG. 7B, each unit can include one or more inlets 181 for transmission of sample droplets and/or process reagents into a unit (e.g., from a reservoir, from an upstream unit). Additionally or alternatively, each unit can include one or more outlets 185 for transmission of processed sample droplets and/or waste material (e.g., into a reservoir, into a downstream unit). As shown in FIG. 7B, a unit can include a sample reservoir 182 and a sample inlet 181 coupled to an upstream portion the unit and in communication with the sample reservoir 182, such that the reservoir 182 can transmit a sample droplet from the sample reservoir 182 into the sample inlet 181 (e.g., by way of a pumping system, by way of capillary action, etc.). Additionally or alternatively, the unit can include a binding reservoir 182' containing a binding fluid and a binding inlet 181' coupled to an upstream portion of the unit and in communication with the binding reservoir 182', such that the reservoir 182' can transmit a binding droplet from the binding reservoir 182' into the binding inlet 181' (e.g., by way of a pumping system, by way of capillary action, etc.). Additionally or alternatively, the unit can include a wash reservoir 182" containing a washing fluid and a wash inlet 181" coupled to an upstream portion the unit and in communication with the wash reservoir 182", such that the reservoir 182" can transmit a wash droplet from the wash reservoir 182" into the wash inlet 181" (e.g., by way of a pumping system, by way of capillary action, etc.). Additionally or alternatively, the unit can include an elution reservoir 182" containing an elution fluid and an elution inlet 181" coupled to an upstream portion the unit and in communication with the elution reservoir 182", such that the reservoir 182" can transmit an elution droplet from the elution reservoir 182" into the elution inlet 181" (e.g., by way of a pumping system, by way of capillary action, etc.).

Additionally or alternatively, in a specific example, the unit can include a waste reservoir 186 and a waste outlet 185 coupled to a downstream portion the unit and in communication with the waste reservoir 186, such that the reservoir 186 can receive a waste droplet from the waste inlet 185 (e.g., by way of a pumping system, by way of capillary action, etc.). Additionally or alternatively, in the specific example, the unit can include a results region 186' and a results outlet 185' coupled to a downstream portion the unit and in communication with the results region 186', such that the reservoir 186' can receive a processed droplet from the unit (e.g., after sample droplet processing) into the results inlet 185 (e.g., by way of a pumping system, by way of capillary action, etc.). In this example, the results region 186' can be configure proximal the optical detection subsystem 170 in order to perform an analysis associated with optical detection.

In these variations, modules of the system 100 can thus be coupled together in a designed configuration, in order to transmit one or more samples from one unit that is adapted for one protocol step (e.g., magnetic separation, sample evaporation, sample thermocycling, sample cooling, washing, etc.), to another module that is adapted for another protocol step (e.g., magnetic separation, sample evaporation, sample thermocycling, sample cooling, washing, etc.), to another module that is adapted for another protocol step (e.g., magnetic separation, sample evaporation, sample thermocycling, sample cooling, washing, etc.), to another module that is adapted for another protocol step (e.g., magnetic separation, sample evaporation, sample thermocycling, sample cooling, washing, etc.), and to any other suitable module(s). As such, each module of the system can include an input region configured to receive samples from an upstream module, and/or an output region configured to transmit samples at various stages of processing to a downstream module. Furthermore, the system 100 can include a set of units, wherein the units of the set of units are reversibly coupleable to each other (or irreversibly coupleable to each other), such that inlets of downstream units are coupled to outlets of upstream units.

In specific examples, each unit can be reversibly coupleable to at least another of the set of units with joints that align an outlet of an upstream unit with an inlet of a downstream unit. However, the modules can be coupled together in any other suitable manner in these variations.

2. Method

Figure 9A:
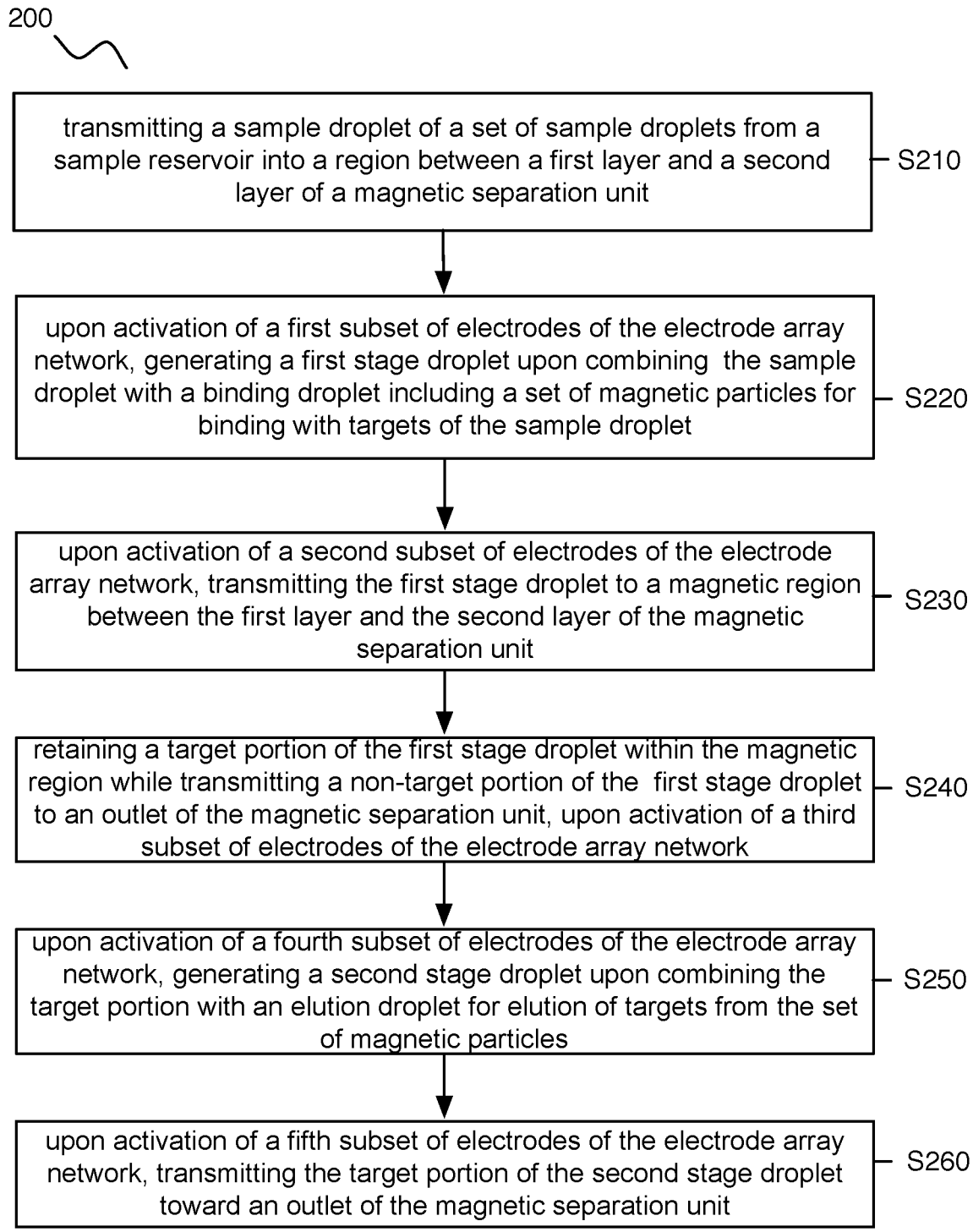
FIGS. 9A-9C depict embodiments and variations of a method implemented by a digital microfluidics system.

As shown in FIG. 9A, a method 200 for sample processing can include: transmitting a sample droplet of a set of sample droplets from a sample reservoir into a region between a first layer and a second layer of a magnetic separation unit S210, wherein the first layer is in communication with an electrode array network configured to provide a pattern of controlled electric fields for manipulation of the set of sample droplets; upon activation of a first subset of electrodes of the electrode array network, generating a first stage droplet upon combining the sample droplet with a binding droplet including a set of magnetic particles for binding with targets of the sample droplet S220; upon activation of a second subset of electrodes of the electrode array network, transmitting the first stage droplet to a magnetic region between the first layer and the second layer of the magnetic separation unit S230; retaining a target portion of the first stage droplet within the magnetic region while transmitting a non-target portion of the first stage droplet to an outlet of the magnetic separation unit, upon activation of a third subset of electrodes of the electrode array network S240; upon activation of a fourth subset of electrodes of the electrode array network, generating a second stage droplet upon combining the target portion with an elution droplet for elution of targets from the set of magnetic particles S250; and upon activation of a fifth subset of electrodes of the electrode array network, transmitting the target portion of the second stage droplet toward an outlet of the magnetic separation unit S260.

The method 200 is preferably implemented using an embodiment, variation, or example of the system 100 described in Section 1 above; however the method 200 can additionally or alternatively be implemented using any other suitable system. As such, in relation to activation or deactivation of subsets of electrodes of the electrode array network, blocks of the method 200 can be implemented by way of an electronics module 150 and a control module 160 for electrode toggling between active and inactive states.

Figure 9B:
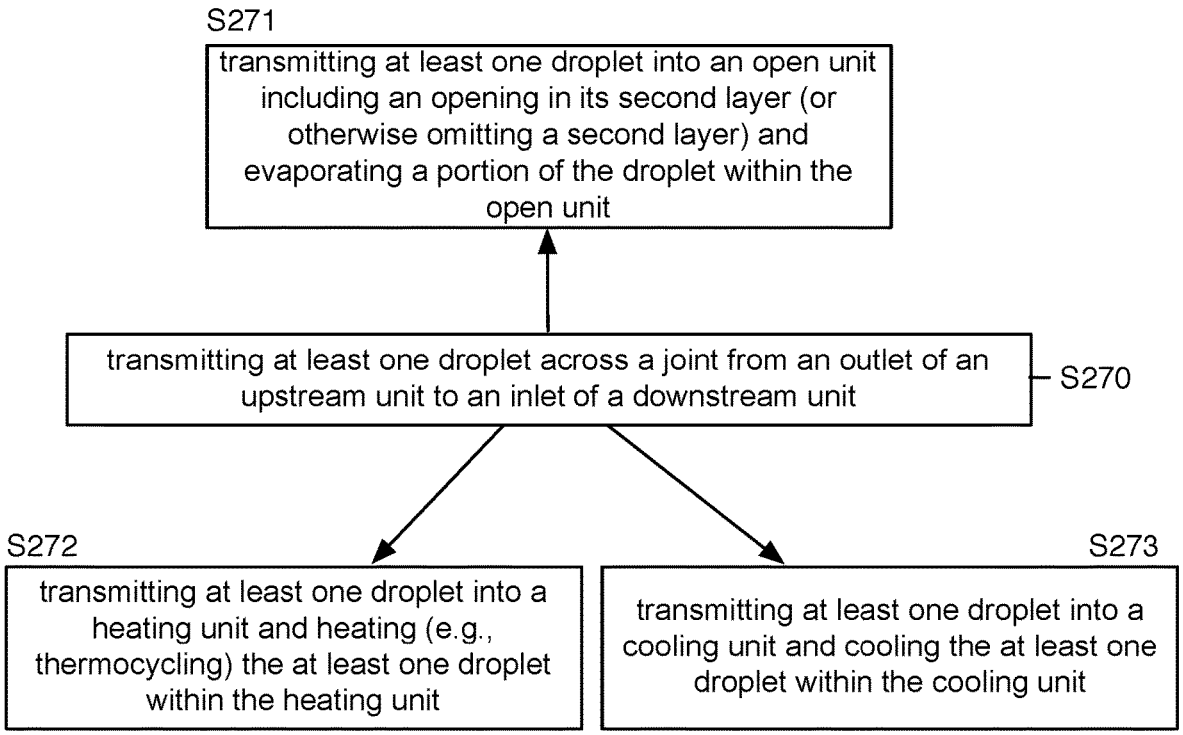

Furthermore, in relation to multiple units of the system 100, wherein units have various configurations and/or functions, the method 200 can additionally or alternatively include: transmitting at least one droplet across a joint from an outlet of an upstream unit to an inlet of a downstream unit S270. In variations, as shown in FIG. 9B, Block S270 can include one or more of: transmitting at least one droplet into an open unit including an opening in its second layer (or otherwise omitting a second layer) and evaporating a portion of the droplet within the open unit S271; transmitting at least one droplet into a heating unit and heating (e.g., thermocycling) the at least one droplet within the heating unit S272; transmitting at least one droplet into a cooling unit and cooling the at least one droplet within the cooling unit S273; and/or transmitting at least one droplet between units in any other suitable manner.

Figure 9C:
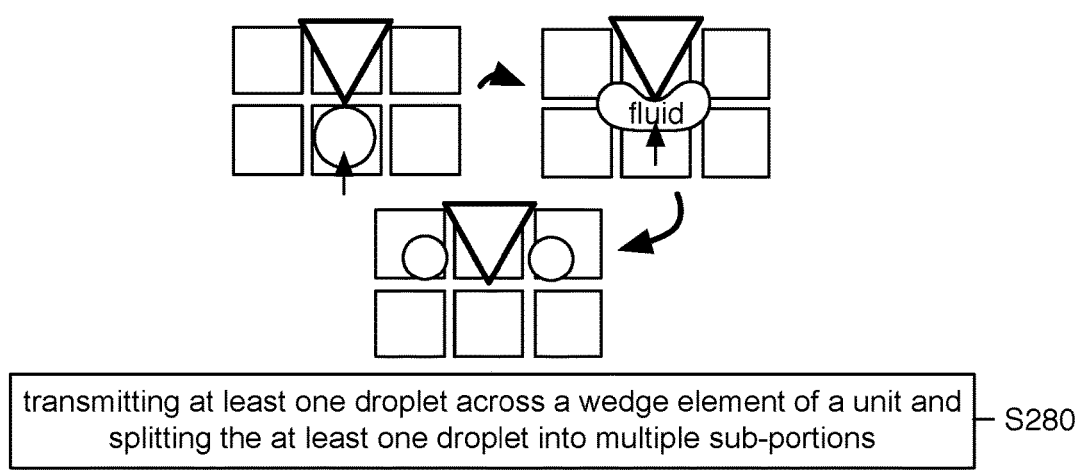

Additionally or alternatively, in relation to a wedge element, as described in Section 1.4 above, the method 200 can include transmitting at least one droplet across a wedge element of a unit and splitting the at least one droplet into multiple sub-portions S280 for further processing, as shown in FIGS. 7A and 9C. However, variations of the method 200 can additionally or alternatively include any other suitable steps or blocks, in relation elements of the system 100 described above, and/or any other suitable system elements.

Figure 5:
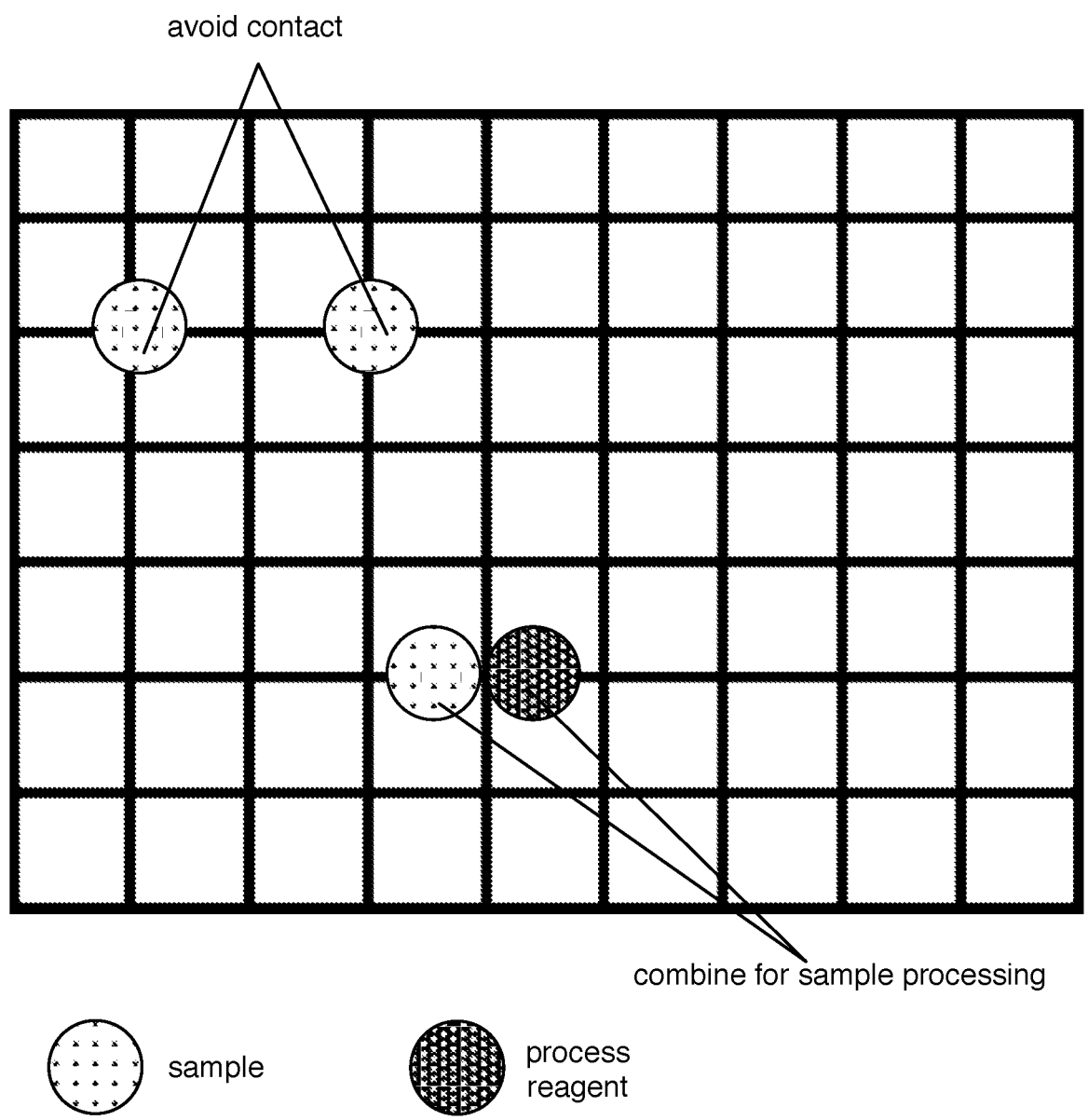
FIG. 5 depicts variations of simultaneous processing of multiple samples, as implemented by an embodiment of a digital microfluidics system.

Furthermore, in relation to the method 200 described above, each sample volume can be transmitted along the same path over the electrodes of the electrode array network in implementation of a sample processing protocol, as described above; however, one or more sample volumes of the set of sample droplets can alternatively be transmitted along a path different from those of other sample volumes (e.g., in implementation of a different sample processing protocol), wherein transmission along different paths is still performed in a manner that avoids sample cross-contamination. As such, the electrode array network 120 and the electronics module 150 are preferably configured such that sample volumes of different samples never coexist proximal the same location of the electrode array network 120 at the same point in time. Process reagents used in sample processing can, however, be promoted to collide or integrate with sample volumes and/or other volumes of processing reagents, by way of the electrode array network 120, as shown in FIG. 5.

In an example operation for a single sample volume, in relation to the method 200 described above, the sample volume can be configured proximal a first electrode/active region of the electrode array network 120 upon toggling of the first electrode to an active voltage state. To transmit the sample volume to an adjacent location, the first electrode can then be toggled to an inactive voltage state in coordination of toggling of a second electrode/active region to an active state, thereby creating a driving force for transmission of the sample volume from the first electrode to the second electrode. Thus, by varying voltage across the electrode array network 120, sample volumes can be transmitted across the electrode array network 120 along controlled paths for sample processing. In expansion of the above description to a set of sample volumes intended to be processed by the system 100, the electrode array network 120 can thus facilitate transmission of the set of sample volumes across the electrode array network 120 in defined paths, in a manner that avoids sample cross-contamination but allows for combination of sample volumes with process reagents.

As indicated above, spacing between electrodes of the electrode array network 120 can be modulated based upon the volumes of the samples being processed, viscosity of the samples being processed (e.g., in terms of an emulsion), and/or any other suitable characteristics of the samples being processed.

Figure 10A:
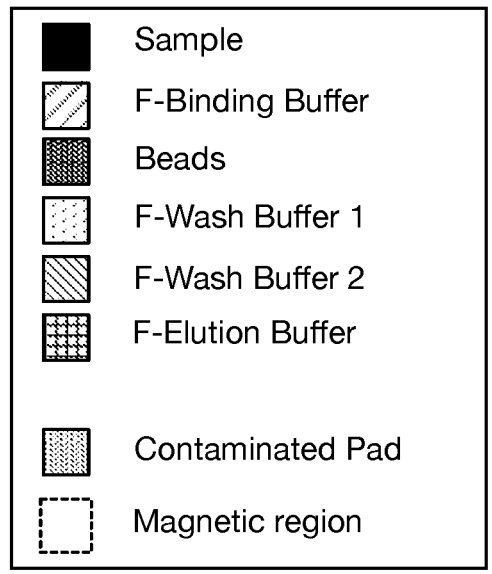
FIGS. 10A-10O depict a specific application of sample processing, implemented by a variation of a digital microfluidics system.
Figure 10B:
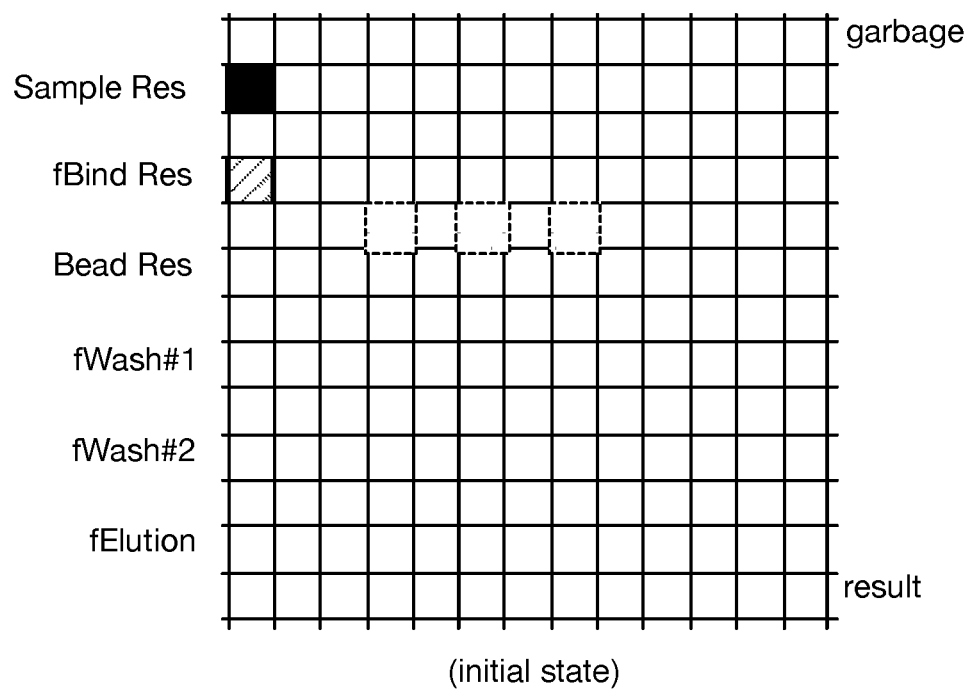
Figure 10E:
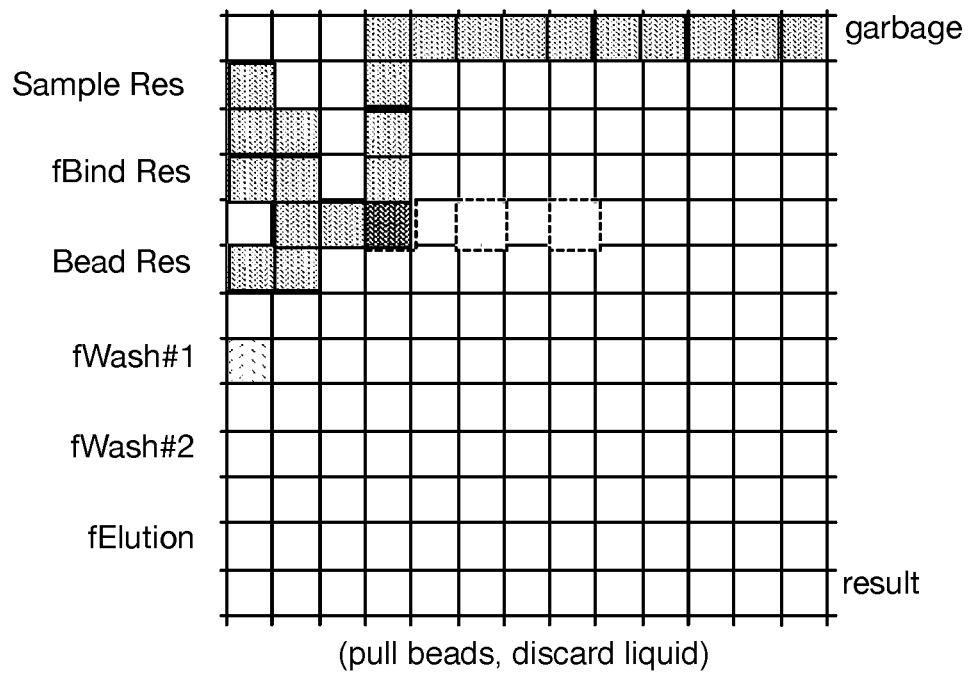
Figure 10F:
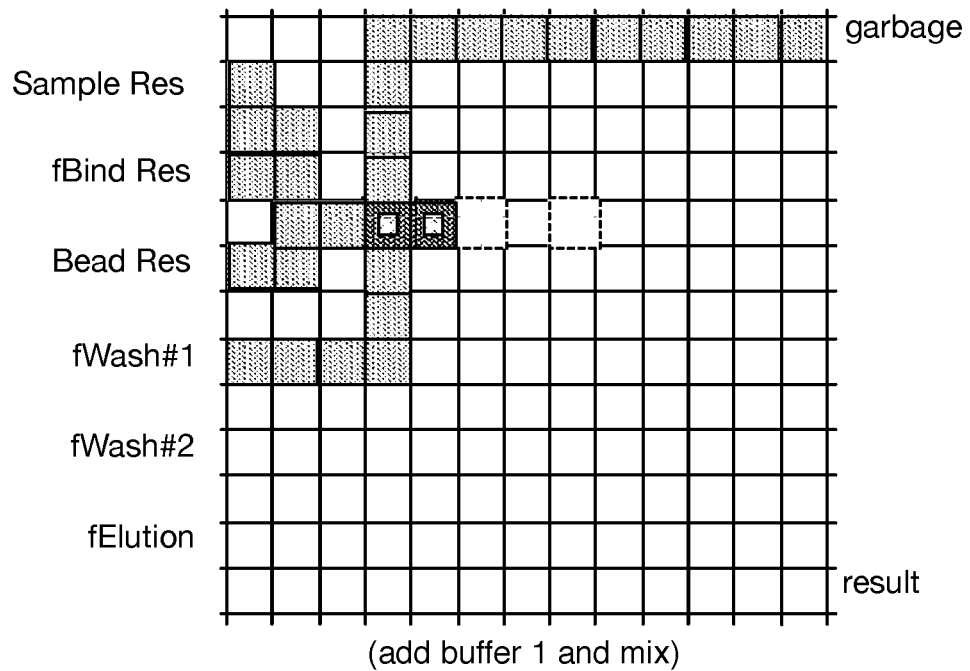
Figure 10G:
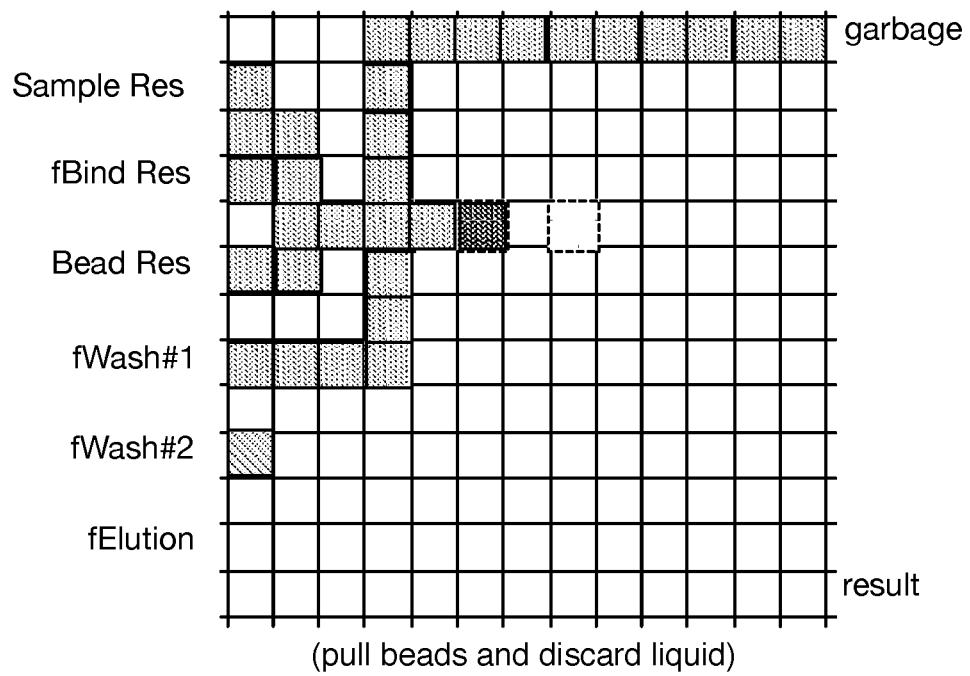
Figure 10H:
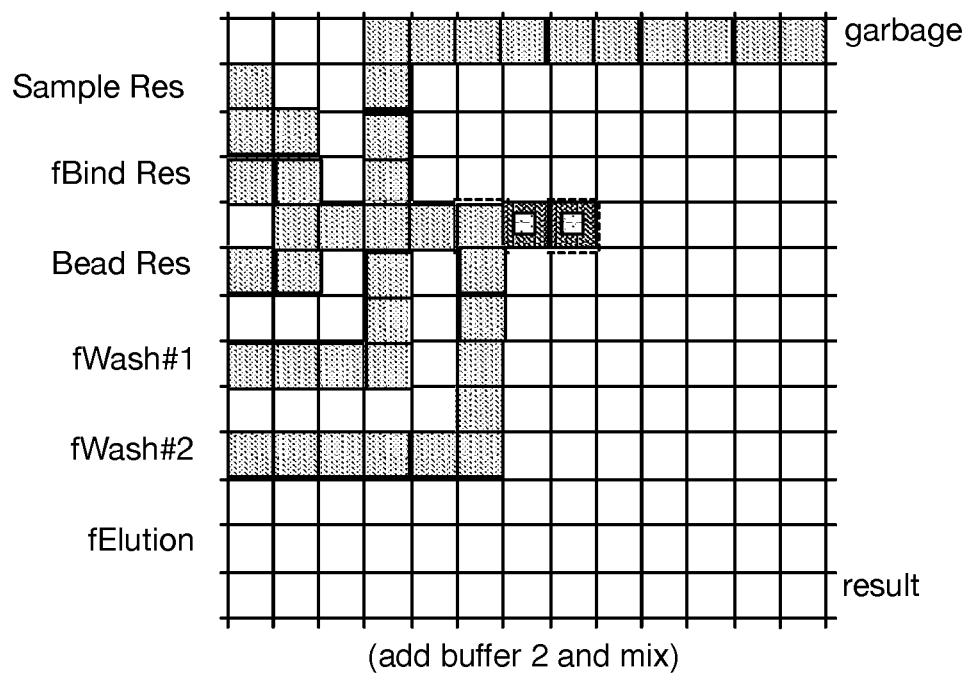
Figure 10I:
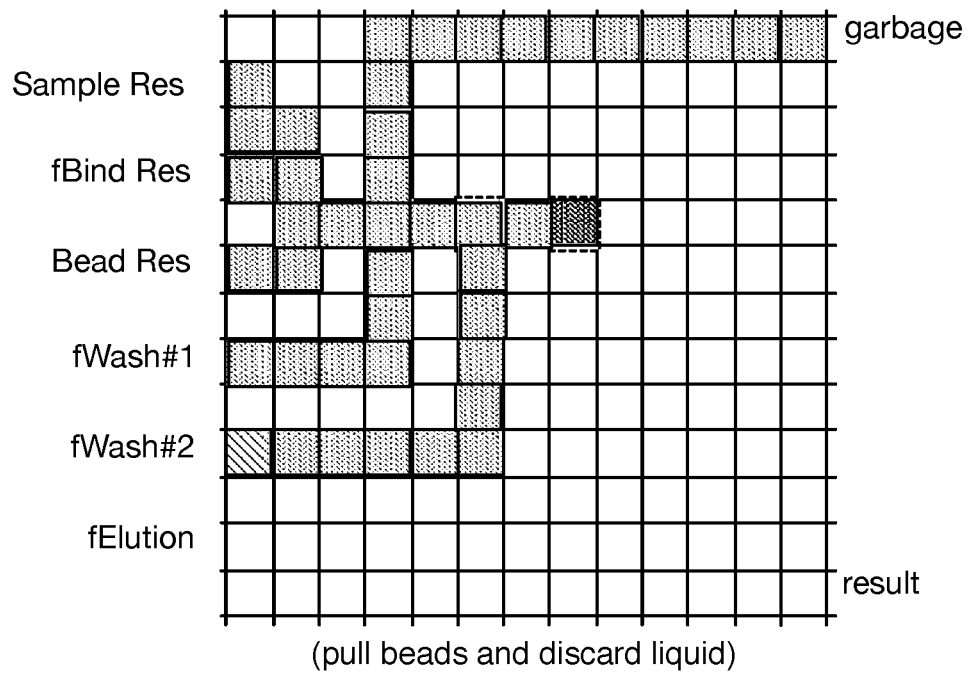
Figure 10J:
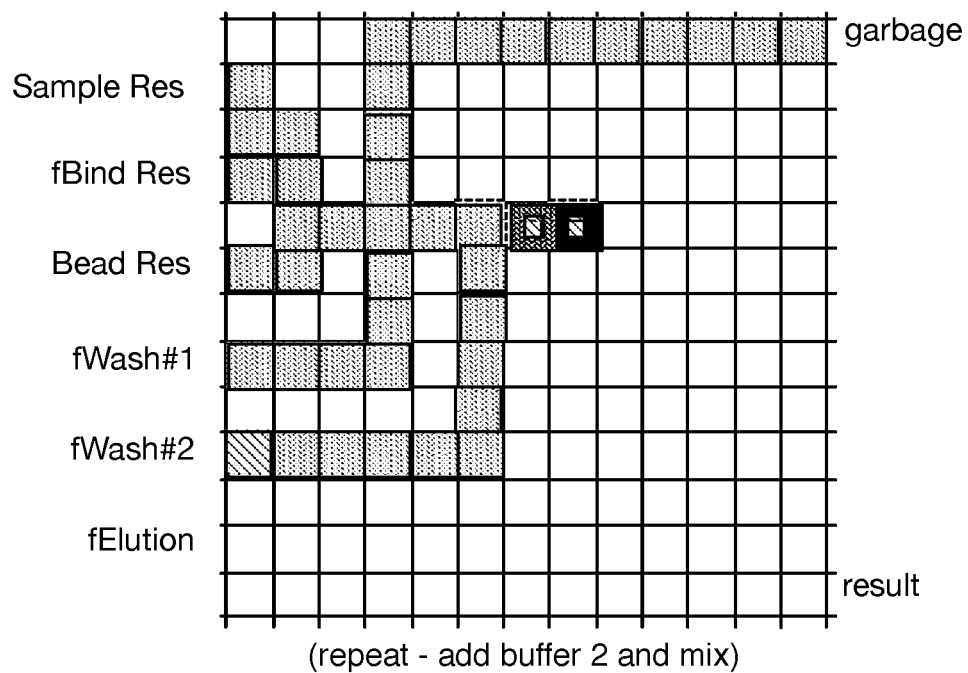
Figure 10K:
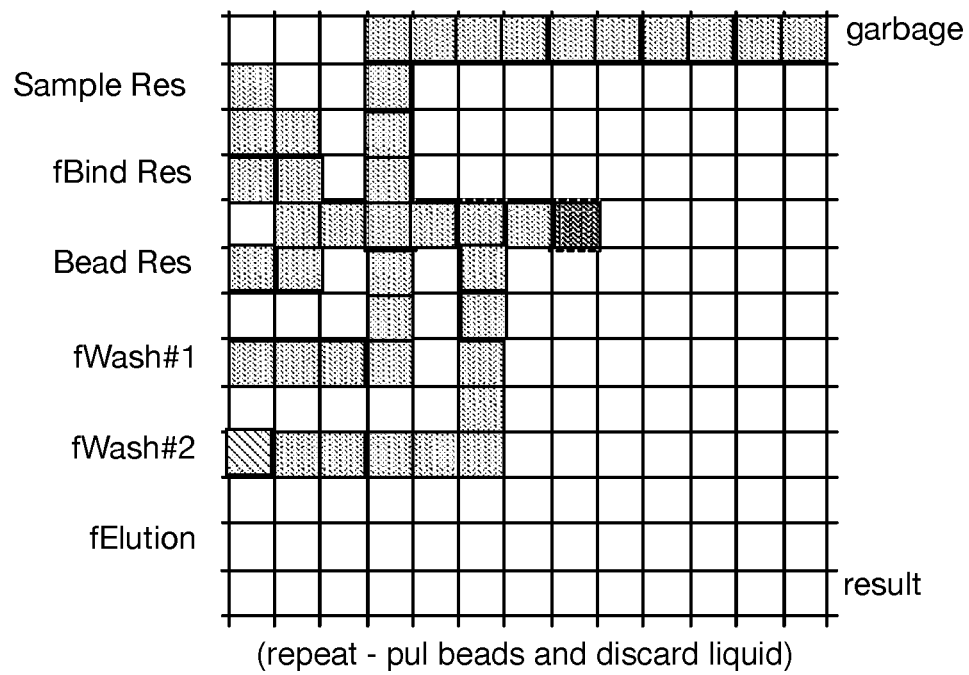
Figure 10L:
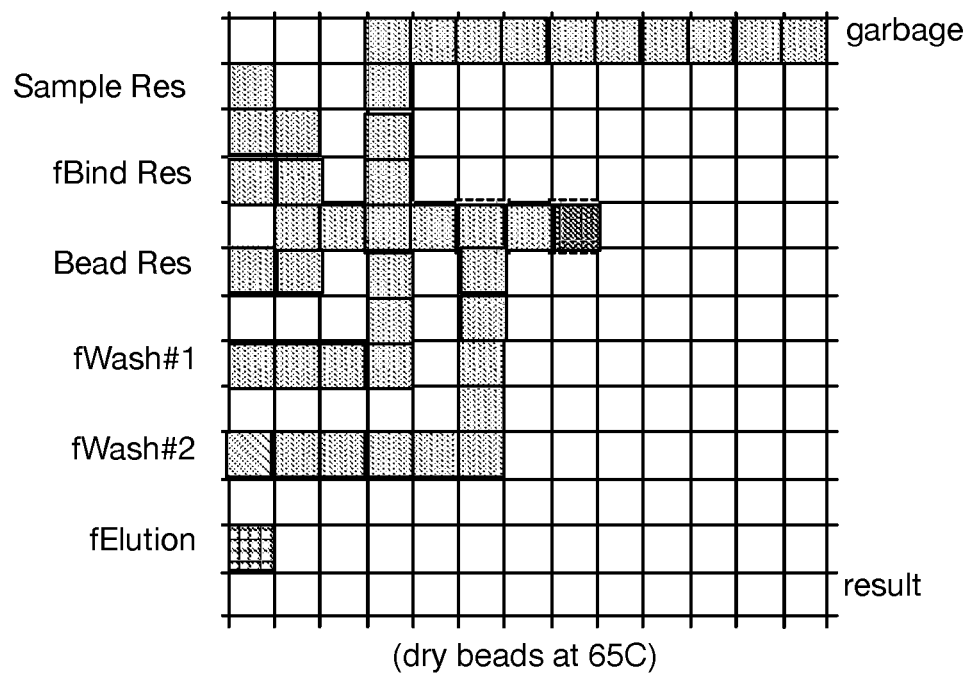
Figure 10M:
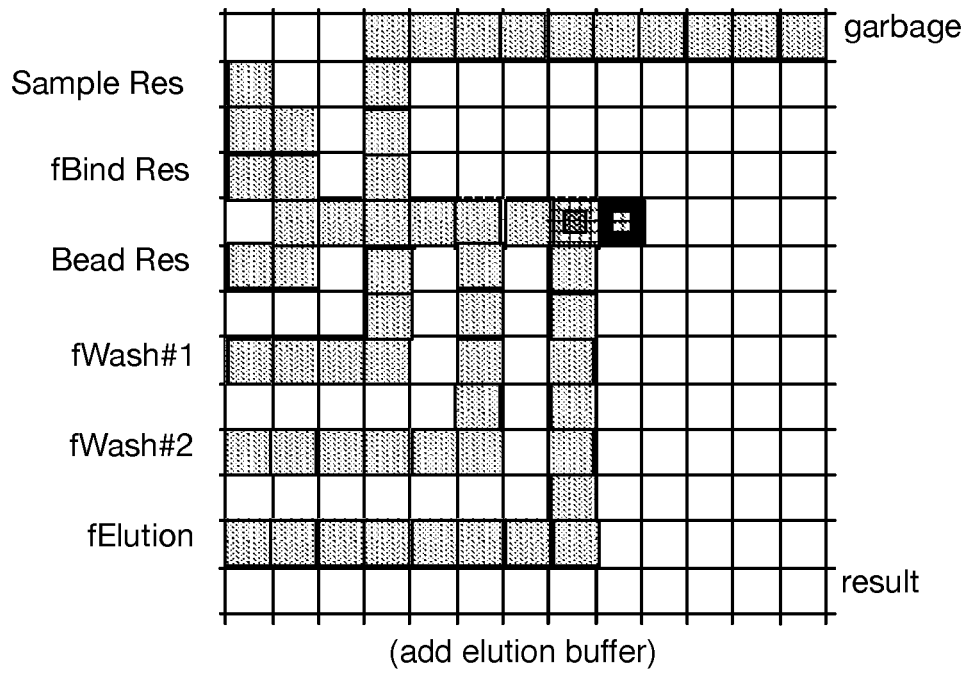
Figure 10N:
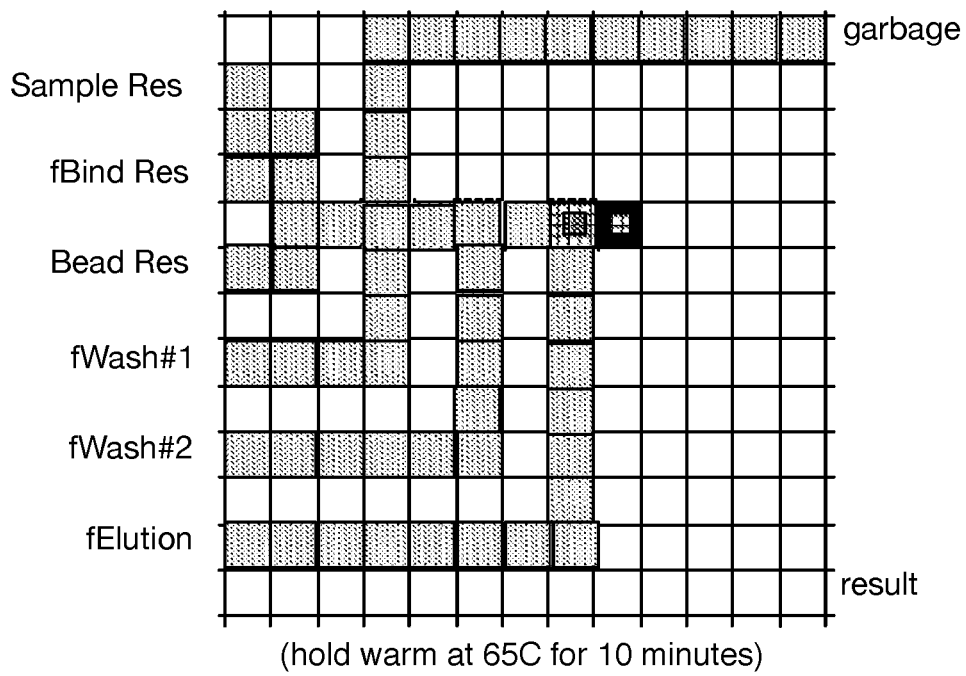
Figure 10O:
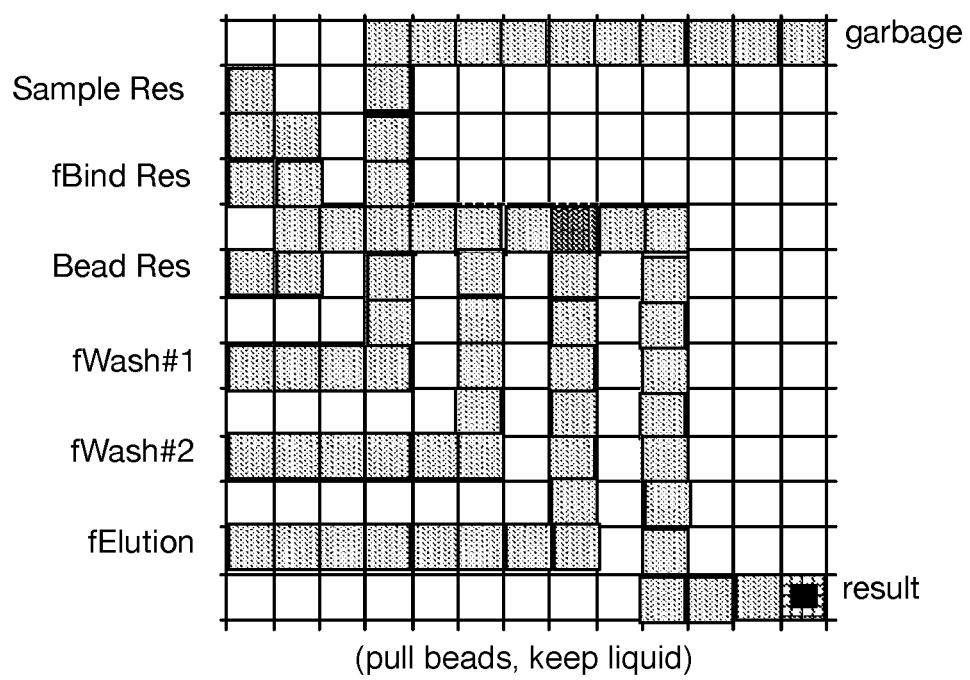

In one specific operation for a sample droplet volume, as shown in FIGS. 10A-10O, a sample droplet volume can be combined and processed with different processing reagents with sequential toggling of electrodes of the set of electrodes 120 in coordination with transmission of sample and process fluids (shown in FIG. 10A) across the system. In more detail, as shown in FIG. 10B, a sample droplet volume and a binding process solution volume can be transmitted into the system and combined (i.e., to create the first stage droplet) upon driving the volumes toward a first active electrode position, as shown in FIG. 10C. Then, as shown in FIGS. 10C and 10D, a solution of magnetic beads can be combined with the sample droplet volume and binding process solutions upon driving the volumes toward a second active electrode position. The processes of FIGS. 10C and 10D can thus be used to bind targets to a set of magnetic beads of the solution of magnetic beads.

Then, as shown in FIG. 10E, the magnetic bead-bound targets can be retained in position (e.g., upon activation of an electromagnet proximal the substrate, upon driving the magnetic bead-bound targets toward a magnetic region of the system 100, etc.), and waste fluid can be driven toward a waste region of the system. As shown in FIGS. 10E and 10F, a first wash buffer volume can then be combined with the magnetic bead-bound targets upon activation of a third active electrode position, the magnetic bead-bound targets can be retained in position (as shown in FIG. 10G), and waste fluid can be driven toward a waste region of the system in a first wash process. As shown in FIGS. 10G and 10H, a second wash buffer volume can then be combined with the magnetic bead-bound targets upon activation of a fourth active electrode position, the magnetic bead-bound targets can be retained in position (as shown in FIG. 10I), and waste fluid can be driven toward a waste region of the system in a second wash process. A third wash process can be performed as in FIGS. 10J and 10K, and then the magnetic bead-bound targets can be dried (e.g., at 65° C.) at an electrode position of the system, as shown in FIG. 10L. Then, as shown in FIGS. 10L and 10M, an elution solution volume can be combined with the dried magnetic bead-bound targets upon driving the elution solution volume toward the dried magnetic bead-bound targets, and incubated (e.g., at 65° C. for 10 minutes) to elute the targets from the set of magnetic beads, as shown in FIG. 10N. Finally, as shown in FIG. 10O, an eluted volume of targets can be driven toward a target output region, while the set of magnetic beads is retained in position at an active magnetic region of the system.

While the above protocol describes a specific application of the system 100, variations of the protocol and/or any other suitable protocol can be implemented using one or more embodiments, variations, and examples of the system 100.

The system 100 and/or method 200 of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:

1. A system for processing a set of sample droplets, the system including:
    a set of units, each unit reversibly coupleable to at least another of the set of units with joints that align an outlet of an upstream unit with an inlet of a downstream unit, each of the set of units including:
    a substrate having a broad surface,
    an electrode array network coupled to the broad surface of the substrate and operably connected to a controller capable of modulating voltage states at each electrode of the electrode array network to provide a pattern of controlled electric fields for manipulation of the set of sample droplets,
    a first layer for separating sample volumes from the electrode array network, the first layer composed of a flexible hydrophobic material in communication with the electrode array network and coupled to the electrode array network with a non-conductive material layer comprising at least one of: an oil layer, an adhesive layer, and a resin layer, and
    a first layer-providing subsystem including a length of the flexible hydrophobic material, wherein the first layer-providing subsystem transmits a portion sub-length of the length of the flexible hydrophobic material into position relative to a fixed position of the electrode array network to form a first layer, in between experimental sample runs of the system,
    wherein a first unit of the set of units comprises an inlet in communication with a sample reservoir and a distribution of magnets aligned proximal to subregions of its electrode array network; and
    wherein at least one of the first unit and a second unit of the set of units comprises a rigid second layer opposing its first layer and displaced from its first layer to define a region wherein droplets of the set of sample droplets reside during sample processing.

2. The system of claim 1, comprising a plurality of sets of units, wherein the plurality comprises the set of units including at least one of the first unit and the second unit, and wherein each unit of the plurality of the set of units comprises a respective substrate, electrode array network, first layer, and first layer-providing subsystem.

3. The system of claim 1, wherein at least one of: the first unit, the second unit, and a third unit of the set of units, comprises a heating element aligned with at least one position of its electrode array network.

4. The system of claim 1, wherein at least one of: the first unit, the second unit, and a third unit of the set of units, includes a wedge element positioned between its first layer and its second layer within a path for physically contacting a sample droplet of the set of sample droplets, wherein, during operation, driving the sample droplet toward a pointed region of the wedge element, upon activation of one or more electrode positions of the electrode array network, physically contacts and splits the sample droplet into at least two portions.

5. The system of claim 1, wherein a second layer of at least one of the first unit and the second unit of the set of units comprises indium tin oxide and is proximal to an optical detection system.

6. The system of claim 1, wherein at least one of the first unit, the second unit, and a third unit of the set of units includes an open region for evaporation of fluid from at least one of the set of sample droplets during operation.

7. The system of claim 6, wherein the open region comprises an opening in the second layer of at least one of the first unit, the second unit, and the third unit.

8. The system of claim 1, further including a binding reservoir, containing a binding reagent, in communication with a binding inlet that transmits the binding reagent between the first layer and the second layer of at least one of the first unit and the second unit.

9. The system of claim 8, further including a wash reservoir, containing a wash reagent, in communication with a wash inlet that transmits the wash reagent between the first layer and the second layer of at least one of the first unit and the second unit.

10. The system of claim 9, further including an elution reservoir, containing an elution reagent, in communication with an elution inlet that transmits the elution reagent between the first layer and the second layer of at least one of the first unit and the second unit.

11. The system of claim 1, further including a waste outlet that transmits waste from at least one of the set of droplets from between the first layer and the second layer of at least one of the first unit and the second unit into a waste reservoir.

12. The system of claim 11, further including a results outlet that transmits processed sample fluid from at least one of the set of droplets from between the first layer and the second layer of at least one of the first unit and the second unit into a detection region.

13. The system of claim 12, further comprising an optical detection subsystem having at least a portion of the set of units within its field of view, wherein the optical detection subsystem performs at least one of: 1) detection of positions of the set of droplets in relation to the set of units of the system and 2) performing an analysis of processed sample fluid at the detection region.

14. The system of claim 1, wherein the first unit comprises a first coupling region and the second unit comprises a second coupling region capable of reversibly coupling the first unit to the second unit, wherein coupling the first unit to the second unit provides fluid communication between a sample outlet of the first unit and a sample inlet of the second unit.

15. The system of claim 1, wherein the first layer-providing subsystem comprises a dispensing spool at a first side of at least one of the first unit and the second unit, the first-layer providing subsystem capable of transmitting the portion sub-length of the flexible hydrophobic material over the substrate relative to the fixed position of the electrode array network, and wherein the first layer-providing subsystem further comprises a collecting spool at a second side of at least one of the first unit and the second unit that collects used flexible hydrophobic material.

16. The system of claim 1, wherein at least one of the first unit, the second unit, and a third unit of the set of units comprises a cooling element aligned with at least one position of its electrode array network.

* * * * *